(12) United States Patent
Mascharak

(10) Patent No.: US 8,609,843 B2
(45) Date of Patent: *Dec. 17, 2013

(54) PHOTOACTIVE METAL NITROSYLS FOR BLOOD PRESSURE REGULATION AND CANCER THERAPY

(75) Inventor: Pradip K. Mascharak, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/420,299

(22) Filed: Mar. 14, 2012

(65) Prior Publication Data
US 2012/0184014 A1 Jul. 19, 2012

Related U.S. Application Data

(60) Continuation of application No. 12/540,810, filed on Aug. 13, 2009, now Pat. No. 8,153,620, which is a division of application No. 11/134,807, filed on May 20, 2005, now Pat. No. 7,582,623.

(60) Provisional application No. 60/573,005, filed on May 20, 2004.

(51) Int. Cl.
*C07F 13/00* (2006.01)
*C07F 15/00* (2006.01)

(52) U.S. Cl.
USPC .................................. 546/2; 546/6

(58) Field of Classification Search
None
See application file for complete search history.

(56) References Cited

U.S. PATENT DOCUMENTS

| 5,631,284 | A | 5/1997 | Legzdins et al. | |
|---|---|---|---|---|
| 6,656,217 | B1 | 12/2003 | Herzog, Jr. et al. | |
| 7,582,623 | B2 * | 9/2009 | Mascharak | 514/185 |

OTHER PUBLICATIONS

Ackroyd et al., "The History of Photodetection and Photodynamic Therapy," *Photochem Photobiol*, 74:656-669 (2001).
Afshar et al., "Syntheses, Structures, and Reactivities of {Fe-NO}[6] Nitrosyls Derived From Polypyridine-Carboxamide Ligands: Photoactive NO-Donors and Reagents for S-Nitrosylation of Alkyl Thiols," *Inorg Chem*, 43:5736-5743 (2004).
Ali et al., "Nitric oxide mediated Photo-induced Cell Death in Human Malignant Cells," *Int J Oncol*, 22:751-756 (2003).
Brëne et al., "Nitric Oxide and Its Role in Apoptosis," *Eur J Pharmacol*, 351:261-272 (1998).
Butler and Megson, "Non-heme Iron Nitrosyls in Biology," *Chem Rev*, 102:1155-1165 (2002).
Clarke and Gaul, "Chemistry Relevant to the Biological Effects of Nitric Oxide and Metallonitrosyls," *Struct Bonding*, 81:147-181 (1993).
Ford and Lorkovic, "Mechanistic Aspects of the Reactions of Nitric oxide with Transition-Metal Complexes," *Chem Rev*, 102:993-1017 (2002).
Ford et al., "Photochemistry of Metal Nitrosyl Complexes: Delivery of Nitric Oxide to Biological Targets," *Coord Chem Rev*, 171:185-202 (1998).
Ghosh et al., "Reactions of NO with Mn(II) and Mn(III) Center Coordinated to Carboxamido Nitrogen: Synthesis of a Manganese Nitrosyl with Photolabile NO," *Inorg Chem*, 43:2988-2997 (2004).
Hoshino et al., "Nitric Oxide Complexes of Metalloporphyrins: An Overview of Some Mechanistic Studies," *Coord Chem Rev*, 187:75-102 (1999).
Hrabie and Keefer, "Chemistry of the Nitric Oxide-Releasing Diazeniumdiolate (Nitrosohydroxylamine) Functional group and Its Oxygen-Substituted Derivatives," *Chem Rev*, 102:1135-1154 (2002).
Keefer, "Biomaterials: Thwarting Thrombus," *Nat Mater*, 2:357-358 (2003).
Koshland, "NO News Is Good News," 258:1862-1865 (1992).
Marlin and Mascharak, "Coordination of Carboxamido Nitrogen to Tervalent Iron: Insight into a New Chapter of Iron Chemistry," *Chem Soc Rev*, 29:69-74 (2000).
Marlin et al., "Carboxamido Nitrogens are Good Donors for Fe(III): Syntheses, Structures, and Properties of Two Low-Spin Nonmacrocyclic Iron(III) Complexes with Tetracarboxamido-N Coordination," *Inorg Chem*, 38:3258-3260 (1999).
Marlin et al., "Spin States and Stability of Fe(III) Complexes of Ligands with Carboxamido Nitrogen and Phenolato Oxygen Donors," *Eur J Inorg Chem*, 859-865 (2002).
Marlin et al., "Chemistry of Iron(III) Complexes of N,N'-bis(2-hydroxyphenyl)-pyridine-2,6-dicarboxamide: Seven-Coordinate Iron(III) Complexes Ligated to Deprotonated Carboxamido Nitrogens," *Inorg Chim Acta*, 297:106-114 (2002).
Mitchel et al., "The Complete Amino Acid Sequence of Papain. Additions and Corrections," *J Biol Chem*, 243:3485-3492 (1970).
Moan and Berg, "Yearly Review: Photochemotherapy of Cancer: Experimental Research," *Photochem Photobiol*, 55:931 (1992).
Noveron et al., "A Synthetic Analogue of the Active Site of Fe-Containing Nitrile Hydratase With Carboxamido N and Thiolate S as Donors: Synthesis, Structure and Reactivities," *J Am Chem Soc*, 123:3247-3259 (2001).
Pandey, "Recent Advances in Photodynamic Therapy," *Porphyrins Phthalocyanines*, 4: 368 (2000).
Patra and Mascharak, "A Ruthenium Nitrosyls That Rapidly Delivers NO to Proteins in Aqueous Solution Upon Short Exposure to UV Light," *Inorg Chem*, 42:7363-7365, (2003).
Patra et al., "The First Non-Heme Iron(III) Complex With a Ligated Carboxamido Group That Exhibits Photolability of a Bound NO Ligand," *Angew Chem Int Ed*, 41:2512-2515 (2002).
Patra et al., "Iron-nitrosyls of a Pentadentate Ligand Containing a Single Carboxamide Group: Syntheses, Structures, Electronic Properties and Photolability of NO," *Inorg Chem*, 42:6812-6823 (2003).
Patra et al., "Photolabile Ruthenium Nitrosyls with Planar Dicarboxamide Tetradentate $N_4$ Ligands: Effects of In-plane and Axial Ligand Strength on NO Release," *Inorg Chem*, 43:4487-4495 (2004).

(Continued)

*Primary Examiner* — Zinna Northington Davis
(74) *Attorney, Agent, or Firm* — Medlen & Carroll, LLP

(57) ABSTRACT

Disclosed are nitric oxide delivery agents and methods of their use, more specifically to photoactive compounds, which are able to perform targeted delivery of nitric oxide in vitro and in vivo and are useful for medicinal applications including, but not limited, to blood pressure regulation and cancer treatment.

8 Claims, 12 Drawing Sheets

(56) References Cited

OTHER PUBLICATIONS

Rowland et al., "Syntheses, Structures, and Reactivity of Low Spin Iron(III) Complexes Containing a Single Carboxamido Nitrogen in a [Fen51] Chromophore," *Inorg Chem*, 40:2810-2817 (2001).

Stochel et al., "Light and Metal Complexes in Medicine," *Coord Chem Rev*, 171:203-220 (1998).

Vega et al., "Nitric Oxide Induces Apoptosis in the Human *Corpus luteum* in vitro," *Mol Human Reprod*, 6:681-687 (2000) Wang et al., "Nitric Oxide Donors: Chemical Activities and Biological Applications," *Chem Rev*, 102:1091-1134 (2002).

Wang et al., "Nitric Oxide Donors: Chemical Activities and Biological Applications," *Chem Rev*, 102:1091-1134 (2002).

Wink et al., "The Multifaceted Roles of Nitric Oxide in Cancer," *Carcinogenesis*, 19:711-721 (1998).

Xu et al., The Role of Nitric Oxide in Cancer, *Cell Res*, 12:311-320 (2002).

PHOTOFRIN (Porfimer Sodium) For Injection, product description, Axcan Scandipharm Inc., Canada, pp. 1-26 (2003).

Afshar et al., "Light-Induced Inhibition of Papain by a $\{Mn\text{-}NO\}^6$ Nitrosyl: Identification of Papain-SnO Adduct by Mass Spectrometer," *J Inorg Biochem*, 99:1458-1464, (2005).

Patra et al., "Reactions of Nitric Oxide with a Low-Spin Fe(III) Center Ligated to a Tetradentate Dicarboxamide N4 Ligand: Parallels between Heme and Non-Heme Systems," *J Am Chem Soc*, 126:4780-4781 (2004).

* cited by examiner $N_a$ = carboxamido N, M = $Fe^{III}$, $Ru^{III}$, $Mn^{II}$ and $Mn^{III}$

A

H₂bpb

B

H₂Me₂bqb

C

PHOTOACTIVE METAL NITROSYLS FOR BLOOD PRESSURE REGULATION AND CANCER THERAPY

This application is a continuation of, and claims priority to, U.S. patent application Ser. No. 12/540,810, filed Aug. 13, 2009, now U.S. Pat. No. 8,153,620, which is a divisional of U.S. patent application Ser. No. 11/134,807 filed May 20, 2005 and issued as U.S. Pat. No. 7,582,623 on Sep. 1, 2009, which claims benefit under 35 U.S.C. §119(e) of provisional U.S. Application No. 60/573,005, filed on May 20, 2004, now abandoned, herein incorporated by reference in its entirety.

FIELD OF THE INVENTION

This invention relates generally to nitric oxide delivery agents and methods of their use, more specifically to photoactive compounds suitable for targeted delivery of nitric oxide. In particular, the compositions and methods of the present invention are suitable for use as vasodilators and as antineoplastic agents.

BACKGROUND OF THE INVENTION

Nitric oxide (NO) is the first gaseous molecule that acts as a biological messenger and participates in a myriad of biological processes including control of blood pressure, neurotransmission and inhibition of tumor growth. The desire to deliver NO at biological targets under specific physiological conditions has inspired research in the area of designed molecules that release NO on demand. Although a few organic exogenous NO donors (like nitrates and nitrosothiols) and sodium nitroprusside (NSP) have been utilized for such purpose, the possibility of non-porphyrin metal nitrosyls as NO donors has not been explored in any systematic way.

The discovery of the roles of nitric oxide (NO) in blood pressure control, neurotransmission, and immune response has stimulated extensive research activity in the chemistry, biology, and pharmacology of NO.[1-5] Cellular NO is almost exclusively generated via oxidation of L-arginine (reaction 1) by the enzyme nitric oxide synthase (NOS).[6] NO synthases are a class of heme-proteins which are both constitutive (e.g., neuronal and endothelial NOS) and inducible (e.g., cytokine-inducible NOS III). The principal targets of NO in bioregulatory processes are also iron proteins. For example, binding of NO to the Fe(II) center of the ferroheme enzyme soluble guanylyl cyclase (sGC) activates the enzyme leading to formation of the secondary messenger cyclic-guanylyl monophosphate (from guanylyl triphosphate), which in turn causes relaxation of smooth muscle tissue of blood vessels. Although NO concentrations of less than 1 mM are involved in endothelium cells for blood pressure control, NO concentrations produced during immune response to pathogen invasion are much higher. Sudden increases in local NO concentration have been exploited in NO-mediated photoinduced death of human malignant cells.[7]

The desire to deliver NO at biological targets under physiological conditions has inspired research in the area of designed molecules that release NO on demand. Several reviews published in the past few years attest the extent of attention and interest in controlled NO release under specific conditions and development of NO-donor compounds.[8] Currently, the major classes of exogenous NO donors include organic nitrates (e.g., glyceryl trinitrate, GTN), nitrites (e.g., isoamyl nitrite, IAMN), nitrosamines, oximes, hydroxylamines, nitrosothiols (e.g., SNAP and GSNO), heterocycles (e.g., SIN-1) and NONOates (e.g., DEA-NO).[8] These compounds (FIG. 1) release NO upon exposure to heat, light, oxidants or thiols, and in some cases via enzymatic reactions. Several of these organic compounds have found use as pharmaceuticals. In addition, metal-NO complexes (nitrosyls) like sodium nitroprusside (SNP) and Roussin's salts have also been exploited as NO donors (FIG. 2).[2,8]

There are however, fundamental problems associated with conventional NO-donors such as GTN, SNAP, IAMN, DEA-NO, as well as the metal-NO complex SNP, when used in biomedical applications. In particular, NO-release is poorly controlled upon administration of these NO-donors to a subject, since NO is released via various enzymatic and non-enzymatic pathways. For example, organic nitrates like GTN have been used to relieve angina pectoris and acute myocardial infraction, while organic nitrites such as isobutyl and isoamyl nitrite have been used clinically as vasodilators. The requirement for specific thiols and/or enzymatic bioactivation for triggering NO release from these drugs renders them less ideal compounds for the generation of predictable rates of NO release. Patients also develop nitrate tolerance in many cases. Nitrosothiols NO-donors such as SNAP and related derivatives are often unstable and production of NO is induced by heat, UV light, certain metal ions, superoxide and selected enzymes. In addition, NO-donors such as like hydroxyureas, hydroxylamines, and SIN-1 (sydnonimines) all require activation by specific enzymes and are difficult to target to a given site.

Production of secondary toxic product(s) is another problem encountered with certain conventional NO-donors. For example, among the inorganic NO-donors, sodium nitroprusside (SNP, marketed as NIPRIDE or NITROPRESS) has been in therapeutic use for quite some time. SNP is widely used in hospitals to lower blood pressure during hypertensive episodes (e.g., heart attacks and congestive heart failures). It is also used to combat vasoconstriction during open-heart surgery. However, cyanide poisoning poses some risk in SNP therapy, and in fact SNP infusion is often discontinued after 10-15 min to minimize cyanide toxicity. Moreover, deaths of several patients that have received SNP therapy have been reported (e.g., Butler and Megson, *Chem Rev,* 102:1155-1165, 2002). The cyanide ions, released during photolysis or in vivo enzymatic reduction of SNP are metabolized in the liver and kidneys by the enzyme rhodanase, which converts $CN^-$ to $SCN^-$. Patients with severe hepatic compromise therefore require strict monitoring of the thiocyanate levels and are often not good candidates for SNP therapy. Synthetic iron-sulfur cluster nitrosyls like Roussin's black salt (RBS, $[Fe_4S_3(NO)_7]^-$), Roussin's red salt (RRS, $[Fe_2S_2(NO)_4]^{2-}$) and $[FeNOS]_4$ (FIG. 2) have also been employed therapeutically. Although photodecomposition of RRS and RBS generates NO, formation of ferric precipitates often limits their use. In addition, RRS exhibits carcinogenic properties.

Thus, what is needed in the art are compositions and methods comprising NO-donors that can be safely administered to subjects (e.g., patients with heart disease or cancer), and whose release of NO can be satisfactorily regulated. The present invention meets this need by providing compositions and methods comprising NO-complexes that release NO upon illumination with low-power light.

SUMMARY OF THE INVENTION

This invention relates generally to nitric oxide delivery agents and methods of their use, more specifically to photoactive compounds suitable for targeted delivery of nitric oxide. In particular, the compositions and methods of the present invention are suitable for use as vasodilators and as antineoplastic agents.

The present invention provides compositions comprising a non-porphyrin metal nitrosyl that releases nitric oxide (NO) upon illumination with light of low radiant power, wherein the porphyrin metal nitrosyl comprises a pentadentate or tetradentate ligand having one or more carboxamido groups, and a group 7 or group 8 transition metal in a +2, +3 or +4 oxidation state. In some embodiments, the transition metal is selected from the group consisting of $Mn^{II}$, and $Ru^{III}$. In some preferred embodiments, when the non-porphyrin metal nitrosyl is an $[LM(NO)_x]^{n+}$ type, L is the pentadentate ligand, M is the transition metal, x is one or two for number of NO ligands, and n is net charge. In other preferred embodiments, when the non porphyrin metal nitrosyl is an $[L'M(NO)_x]^{n-}$ type, L' is the tetradentate ligand, M is the transition metal, x is one or two for number of NO ligands, and n is net charge. In some preferred embodiments, the ligand comprises one or more pyridine rings. In a subset of these embodiments, the ligand is selected from but not limited to the group consisting of $PaPy_3H$, $PaPy_2OH_2$, $PaPy_2SH_2$, $PcPy_2OH_2$, $PcPy_2SH_2$, $PcPy_3H$, $^{Me}PcPy_3H$, $PaBOH_4$, $PaBSH_4$, $PcBOH_4$, $PcBSH_4$, $Py_2PSH$, $^{Me}PyPSH_4$, $H_2$ bpb, and $H_2Me_2bqb$. Specifically, in some embodiments, the present invention provides compositions comprises a non-porphyrin metal nitrosyl selected from the group consisting of $[(PaPy_3)Ru(NO)](BF_4)_2$, $[(PaPy_3)Mn(NO)]ClO_4$, $[(bpb)Ru(NO)(Cl)]$, $[(Me_2bqb)Ru(NO)(Cl)]$, $[(Me_2bqb)Ru(NO)(py)]$, $[(Me_2bqb)Ru(NO)(Cl)]$, $[(PcPy_3)Fe(NO)](ClO_4)_2$, and $[(MePcPy_3)Fe(NO)](ClO_4)_2$. In some embodiments, the light comprises ultraviolet light and the low radiant power is in the range of 1 to 50 mWatts, while in others, the light comprises visible light and the low radiant power is in the range of 25 to 250 Watts. Compositions comprising a non-porphyrin metal nitrosyl of the present invention are formulated with a physiologically acceptable excipient, in some embodiments. In some preferred embodiments, the non-porphyrin metal nitrosyl is a salt.

In addition, the present invention provides methods of synthesizing a metal nitrosyl comprising: deprotonating a ligand in a solvent to produce a deprotonated ligand, wherein the ligand is a pentadentate or tetradentate ligand having one or more carboxamido groups; reacting a metal salt with the deprotonated ligand to produce a solution comprising an intermediate, wherein the metal is a group 7 or group 8 transition metal in a +2, +3 or +4 oxidation state; and passing NO through the solution to produce a metal nitrosyl. In some embodiments, the transition metal is selected from the group consisting of $Mn^{II}$, and $Ru^{III}$. In some preferred embodiments, the ligand is selected from the group consisting of $PaPy_3H$, $PaPy_2OH_2$, $PaPy_2SH_2$, $PcPy_2OH_2$, $PcPy_2SH_2$, $PcPy_3H$, $^{Me}PcPy_3H$, $PaBOH_4$, $PaBSH_4$, $PcBOH_4$, $PcBSH_4$, $Py_2PSH$, $^{Me}PyPSH_4$, $H_2$ bpb, and $H_2Me_2bqb$.

Moreover, the present invention provides methods of inducing cGMP production by a muscle cell, comprising: providing a composition comprising a non-porphyrin metal nitrosyl; and contacting a muscle cell with the composition under conditions suitable for causing the muscle cell to produce cGMP. In some embodiments, the conditions comprise illuminating the muscle cell with ultraviolet light to cause the metal nitrosyl to release NO. In other embodiments, the conditions comprise illuminating the muscle cell with visible light to cause the metal nitrosyl to release NO. In some preferred embodiments at least ten fold more cGMP is produced when the conditions comprise illumination of the muscle cells with ultraviolet or visible light.

The present invention also provides methods of inducing vasorelaxation of a muscle, comprising: providing a composition comprising a non-porphyrin metal nitrosyl; and contacting a contracted muscle with the composition under conditions suitable for causing the muscle to relax. In some embodiments, the conditions comprise illuminating the muscle with ultraviolet light to cause the metal nitrosyl to release NO. In other embodiments, the conditions comprise illuminating the muscle with visible light to cause the metal nitrosyl to release NO.

Furthermore, the present invention provides methods of administering a concentrated NO burst. The methods comprise: providing a device comprising a catheter having a non-porphyrin metal nitrosyl immobilized at its distal end and a fiber optic line, wherein the fiber optic line is suitable for delivering light to the distal end of the catheter; inserting the catheter into a subject so as to position the distal end in proximity to a site of interest; and illuminating the non-porphyrin metal nitrosyl with light of low radiant power through the fiber optic line, under conditions suitable for causing the metal nitrosyl to release NO. In some embodiments, the subject is a cancer patient and the site of interest is a solid tumor. In preferred embodiments, the solid tumor is selected from the group consisting of a sarcoma, a carcinoma, and a lymphoma.

Additionally, the present invention provides methods of producing a nitrosylated compound, comprising: providing a non-porphyrin metal nitrosyl; contacting a compound having a free thiol group with the non-porphyrin metal nitrosyl under conditions suitable for causing S-nitrosylation of the free thiol to produce a nitrosylated compound. In preferred embodiments, the conditions comprise maintaining temperature in a range of 4° C. to 42° C. In some embodiments, when the non-porphyrin metal nitrosyl is $[(PaPy_3)Ru(NO)](BF_4)_2$, and the conditions comprise illumination with light of low radiant power, the light comprises ultraviolet light and the low radiant power is in the range of 1 to 50 mWatts. In other embodiments, when the non-porphyrin metal nitrosyl is selected from the group consisting of $[(PaPy_3)Fe(NO)](ClO_4)_2$, $[(PcPy_3)Fe(NO)](ClO_4)_2$, and $[(MePcPy_3)Fe(NO)](ClO_4)_2$, the conditions comprise an absence of light. In some preferred embodiments, the compound having a free thiol group is a protein, while in some particularly preferred embodiments the protein is a cysteine protease.

Also provided by the present invention are methods of inhibiting a cysteine protease, comprising: providing a non-porphyrin metal nitrosyl; contacting a cysteine protease with the non-porphyrin metal nitrosyl under conditions suitable for causing inhibition of the cysteine protease. In some preferred embodiments, the conditions comprise illumination with ultraviolet or visible light. Preferably, the conditions comprise ambient temperature (e.g., 20° C.-25° C., preferably 21° C.-23° C.). In preferred embodiments, the illumination causes the metal nitrosyl to release NO to form a cysteine protease-SNO adduct. In some embodiments, the non-porphyrin metal nitrosyl is $[(PaPy_3)Mn(NO)]ClO_4$.

BRIEF DESCRIPTION OF THE FIGURES

FIG. 7(A) provides a plot of $K_{NO}$ values versus light power. Increase in $A_{550}$ of a solution of $[(PaPy_3)Fe(NO)](ClO_4)_2$ in MeCN upon illumination with a 60 W tungsten lamp (Patra et al., *Inorg Chem*, 42:6812-6823, 2003), $K_{NO}$ ($\times 10^3$ s$^{-1}$)=5.60±0.014. FIG. 7(C) provides a graph showing the photodissociation of NO from $[(PaPy_3)Mn(NO)]ClO_4$ in MeCN under aerobic conditions (50 W tungsten lamp, $t_{1/2}$=52 s; Patra et al., *Inorg Chem*, 43:4487-4495, 2004, herein incorporated by reference).

DETAILED DESCRIPTION OF THE INVENTION

Figure 1:
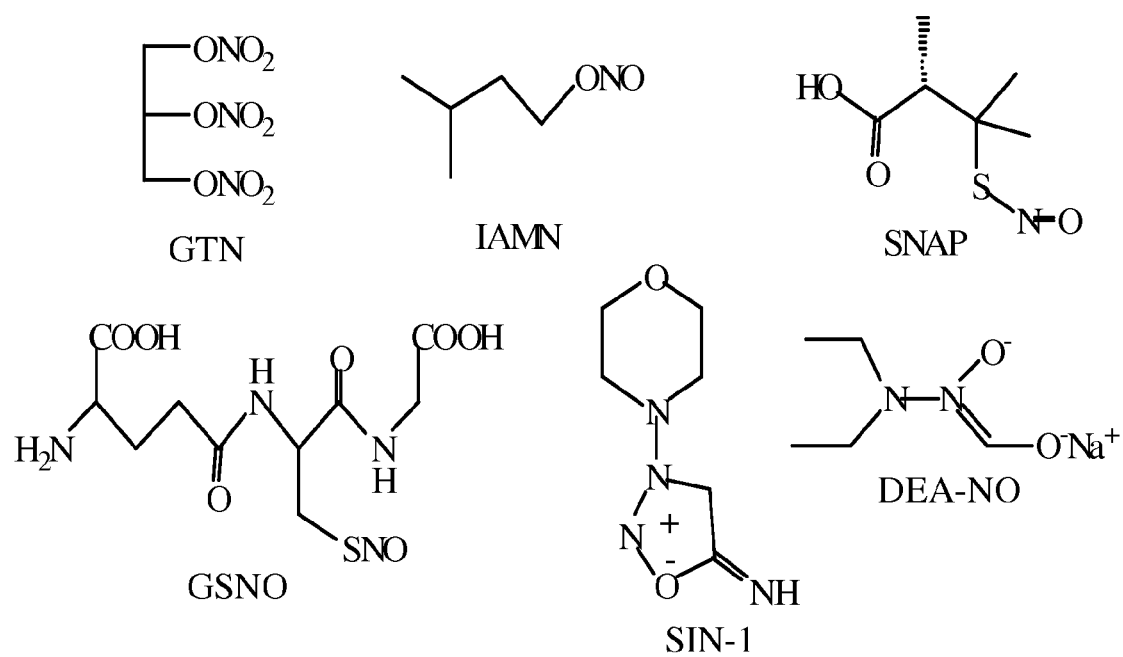
FIG. 1 shows structures of various conventional organic NO donors.
Figure 2:
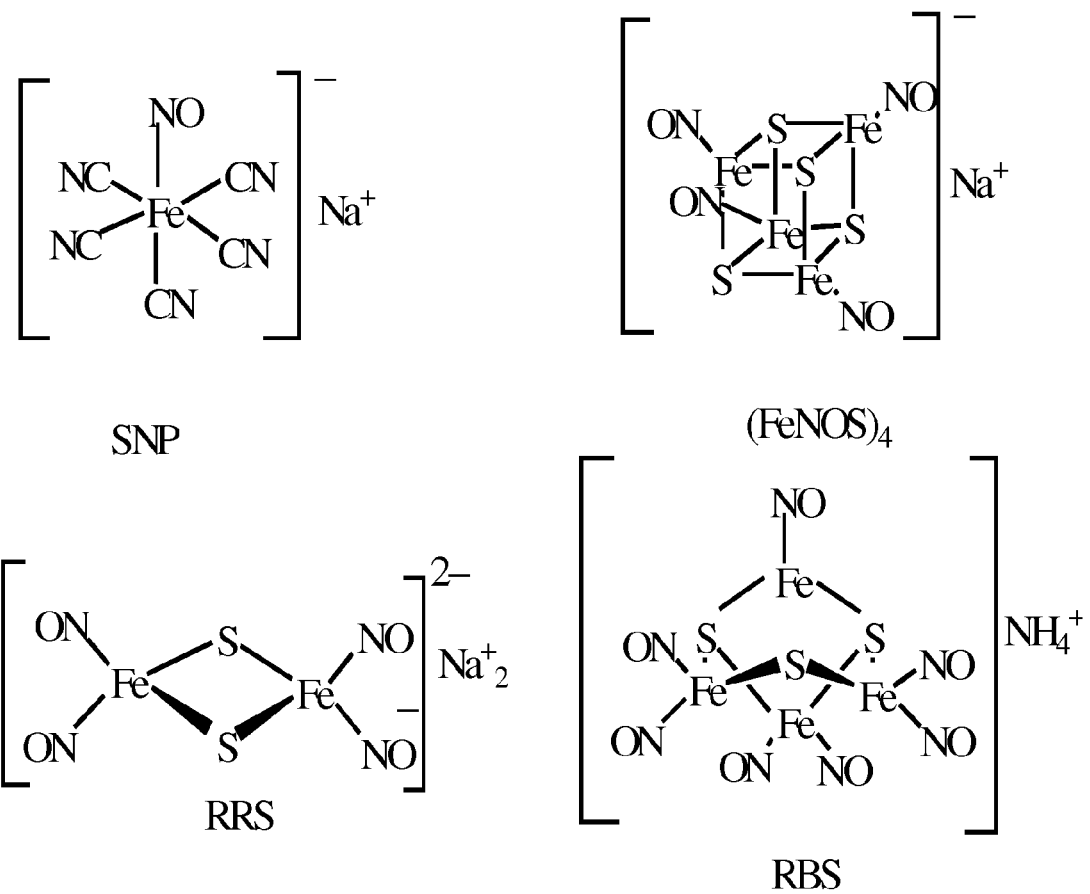
FIG. 2 shows structures of various non-heme iron nitrosyl NO donors.

Although research to date strongly suggests that metal nitrosyls belong to a promising class of NO donors that can provide NO under various conditions including exposure to light,[2,8,9] synthetic strategies that allow one to prepare designed photoactive inorganic NO donors that can be used under very mild illumination, have only recently been described. In particular, the inventor has synthesized a series of non-porphyrin metal nitrosyls (Patra et al., *Angew Chem Int Ed*, 41:2512-2515, 2002, and as described herein). These metal nitrosyls, derived from designed ligands, exhibit rapid release of NO in solution upon illumination with light of low-to-moderate intensity. Since there is no back reaction (NO capture), they exhibit very high quantum efficiency (e.g., very efficient NO-donors). Initial studies have indicated that these metal nitrosyls deliver NO to heme and non-heme proteins such as myoglobin, cytochrome c oxidase and lipoxygenase. Thus, the metal nitrosyls of the present invention are suitable for modulating the activities of specific enzymes.

In addition, preliminary studies have shown that these metal nitrosyls increase the cellular concentration of cyclic GIMP (c-GMP) in rat aortic smooth muscle cells upon illumination. Moreover, rat aortic rings display relaxation when treated with the metal nitrosyls of the present invention under light, while in the dark no such reaction is observed. Thus, some embodiments of the present invention provide photoactive metal nitrosyls for smooth muscle relaxation (and blood pressure control). Methods for testing this activity are known in the art (e.g., U.S. Pat. No. 5,631,284, herein incorporated by reference in its entirety). Unlike conventional NO donors, the NO donors of the present invention release NO under mild conditions when triggered by light. In addition, since sudden surges of NO can cause cell death, the use of the metal nitrosyls in photodynamic therapy for treatment of cancer is contemplated.

The NO donors of the present invention were designed on the basis of several key principles, and as such these principles can be applied to various synthetic protocols for production of photoactive NO donors. The metal nitrosyls described herein are soluble in water, alcohols and solvents such as acetonitrile and DMF, and hence their delivery to biological systems can be altered with ease. Since one can move the absorption maximum of a specific metal nitrosyl by altering the nature of the ligand around the metal as described in more detail below, the wavelength dependence of these NO donors can be controlled by synthetic manipulations of the ligand that is bound to the metal (and which also binds NO).

I. New Non-Porphyrin Metal Nitrosyls

The non-porphyrin metal nitrosyls described herein are suitable for use as NO donor under mild conditions. The inorganic photo-induced NO donors are preferably mononuclear, preferably M(III) (i.e., a metal in its +3 oxidation state) complexes of the type $[LM^{III}(NO)_x]^{n+}$ and $[L'M^{III}(NO)_x]^{n-}$ where L and L' are pentadentate and/or tetradentate ligands with one or more carboxamide groups, the metal is preferably Fe, Mn, or Ru, and x=1 or 2 for the number of NO ligands. In selected cases, nitrosyls with these metal ions in +2 and +4 oxidation states have also been isolated, such that complexes comprising metals in these oxidation states are also contemplated. Metals other than iron, manganese and ruthenium may also be used (preferably transition metals). Preferred metals form a complex, which exhibits sufficient stability and photolability of an NO ligand to be useful for one or more of the purposes described herein. Nitrosyl complexes having more than one metal center are also contemplated.

II. Synthetic Principles

In preparing certain complexes according to preferred embodiments, several principles appear to contribute to preferred properties. It is noted however, that a complex need not exhibit the structural properties corresponding to all or any of these principles to be suitable for use with the compositions and methods of the present invention.

Figure 3:
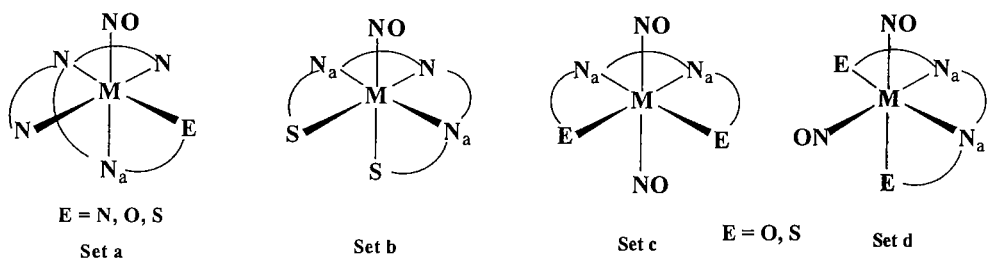
FIG. 3 shows general structures of four target metal nitrosyls of the present invention ($N_a$=carboxamido N, M=$Fe^{III}$, $Ru^{III}$, $Mn^{II}$ and $Mn^{III}$).
Figure 3:
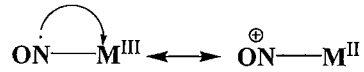

One principle is that NO bound to a metal center, preferably M(III) where M=Fe, Mn, and/or Ru, with relatively high reduction potential exhibits photolability. Coordination of one or more carboxamido nitrogens provides significant stability to the +3 oxidation state of iron[10] (and Mn and Ru). The ligands according to preferred embodiments as disclosed herein generally have one or more carboxamido nitrogens ($N_{amido}$ is abbreviated as $N_a$). A stabilized M(III) center resists total internal transfer of the single electron of NO to iron and helps to keep the equilibrium 1 more on the left hand side of the reaction shown in FIG. 3. NO labilization then results from population of a dissociative excited state. Also, a high reduction potential of the M(III) center allows the metal complex to survive in presence of reductants.

Another principle is that the M(III) center is in low spin to aid in resisting ligand dissociation subsequent to NO loss upon illumination. It is known that reduction and subsequent ligand loss results in the cyanide toxicity and Prussian blue (and other precipitate) formation in case of nitroprusside (SNP) therapy.[8g] Complexes having polydentate strong-field ligands (hence low spin) with high reduction potentials, such as certain complexes according to preferred embodiments herein, generally avoid such problems. Laboratory results have shown that a combination of carboxamido nitrogens and thiolato sulfurs (or ring nitrogens) give rise to low spin M(III) complexes, while incorporation of one or two phenolato oxygens results in high spin species.[10]

Yet another principle is that a strong trans-labilizing group (preferably negatively charged) occupying a position trans to a bound NO molecule results in enhanced photolability of NO in the complex. The presence of this negative charge discourages transfer of the single electron of NO to the metal center and once again the equilibrium stays on the left. The ligands of FIG. 3 all provide such a negatively charged donor trans to the bound NO in the resulting complexes. The only exception is set c in which two NO molecules are trans to each other. This particular set demonstrates the impact of the negative charge since NO is a strong translabilizing yet neutral ligand and hence is different from the thiolato S and phenolato O donors.

III. Designed Ligands

Figure 4:
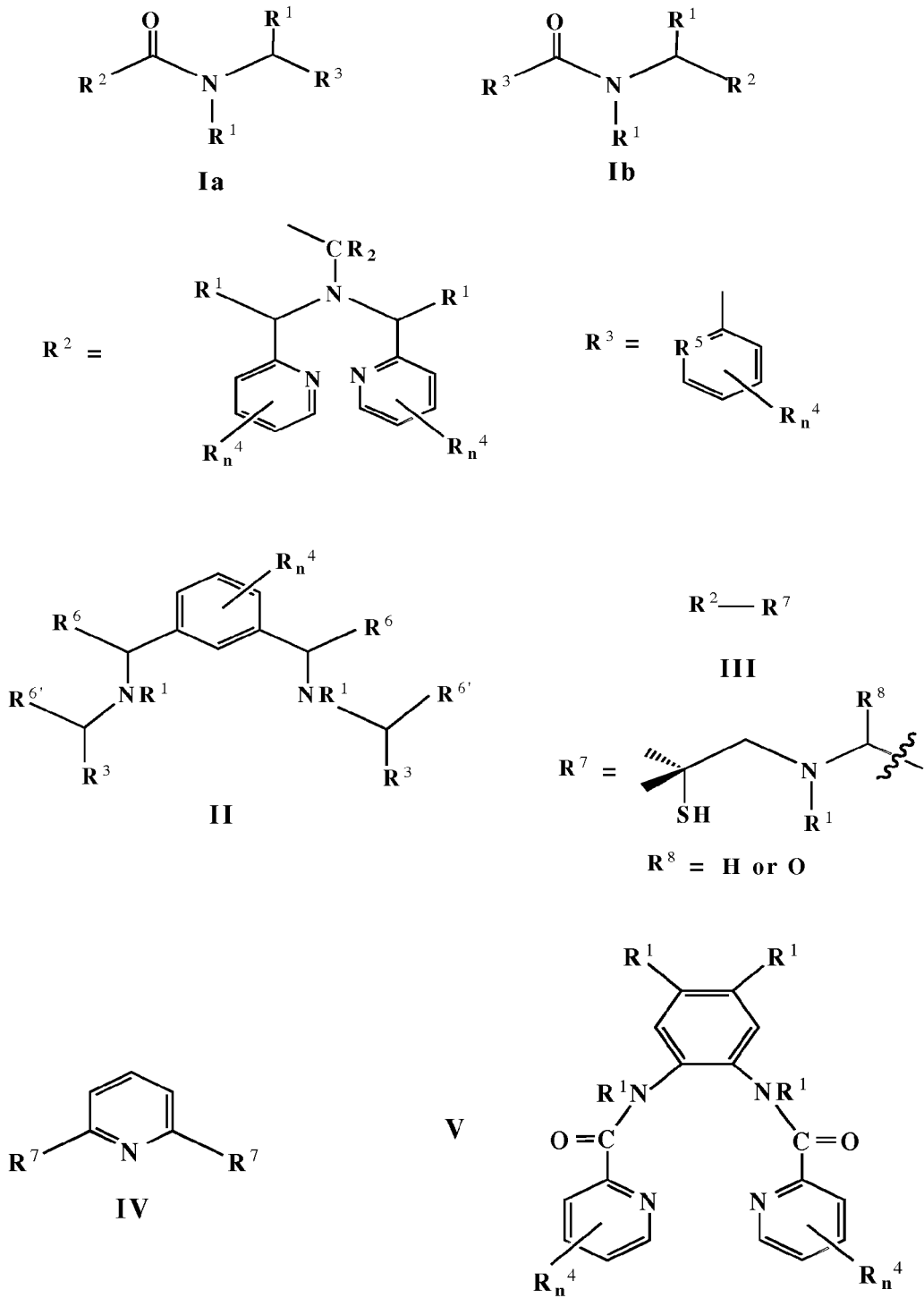
FIG. 4 shows general structures of exemplary carboxamido ligands.

Ligands in accordance with the disclosure herein include those having the structures shown in FIG. 4 as Formulae I-V. $R^1$ is either hydrogen or alkyl. $R^4_n$ is a non-hydrogen substituent replacing a hydrogen atom attached to a ring carbon, and is selected from alkyl, alkoxy, nitro, cyano, halo, hydroxy, mercapto, thioalkoxy, carboxyl, amino, alkyl-substituted amino, aryl and vinyl benzene unit (polymerizable) and n=0-4. In one embodiment, $R^4$ is an electron-withdrawing group. $R^5$ is selected from N, C—OH, C—SH, C—OR', and C—SR$^1$, while $R^6$ and $R^{6'}$ are =O and H, provided that when $R^6$ is =O, $R^{6'}$ is H, and when $R^6$ is H, $R^{6'}$ is =O. Pharmaceutically acceptable salts, solvates or prodrug derivatives of the foregoing compounds are also presently contemplated.

Figure 5:
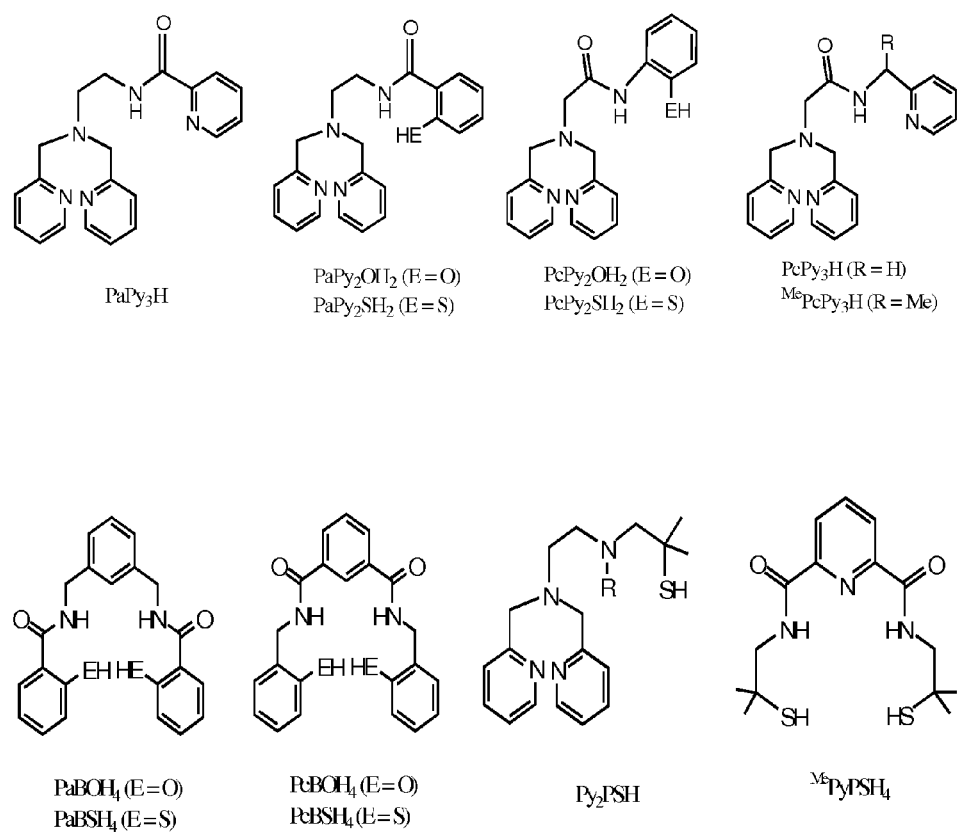
FIG. 5 shows structures of several preferred (designed) carboxamido ligands of the present invention. Various substituents on the phenyl rings are contemplated in some embodiments.

Some pentadentate and tetradentate ligands used in accordance with preferred embodiments are shown in FIG. 5. Although not directly illustrated in FIG. 5 (yet illustrated in the formulae of FIG. 4), one or more carbons and/or nitrogens may be substituted with atoms or groups other than H, preferably methyl or other lower alkyl, methoxy or other alkoxy, nitro, and other, preferably electron withdrawing, groups. Also the ligands of FIGS. 4 and 5 having fused rings may be modified to change the conjugation so as to move $\lambda_{max}$ to a desired wavelength. Note that in the ligands shown, it is also possible to switch the relative positions of the nitrogen and keto portions of the carboxamido group.

These polydentate ligands have one or more built-in carboxamide groups (except for Py$_2$PSH) to ensure low spin metal complexes, preferably having relatively high reduction potentials (Hs denote dissociable amide, phenolic and thiolate proton(s) in each abbreviation). These polydentate ligands help resist formation of multiple [ML$_n$L'$_m$(solv)] species in solution as is the case with nitroprusside (SNP). In addition, most of the metal complexes of these ligands are soluble in water and yet do not form oxo- and hydroxo-bridged polymeric products particularly in case of the iron complexes.[8] The pentadentate ligands like PaPy$_3$H and Py$_2$PSH allow formation of [(L)M(NO]$^{n+}$ or [(L)M(NO]$^{n-}$ species with different donor centers trans to NO. These ligands also give rise to complexes with different ring sizes and different extent of conjugation (compare PaPy$_3$H and PcPy$_3$H). Also, the spin states and redox potentials of the metal centers in the resulting metal complexes with such ligands vary to a great extent as do their electronic absorption spectra. These flexibilities allow one to study the effects of such variations on NO photolability, and accordingly to alter the NO photolability as desired. The tetradentate ligands like PaBOH$_4$ and PcBSH$_4$ have been designed to afford [(L)M(X)(NO)]$^{n-}$ species. In these types of nitrosyls, one can vary the fifth ligand X and check the effect of the trans ligand on NO photolability quite easily.

IV. Photolability of the Bound No Under Mild Conditions

Figure 6:
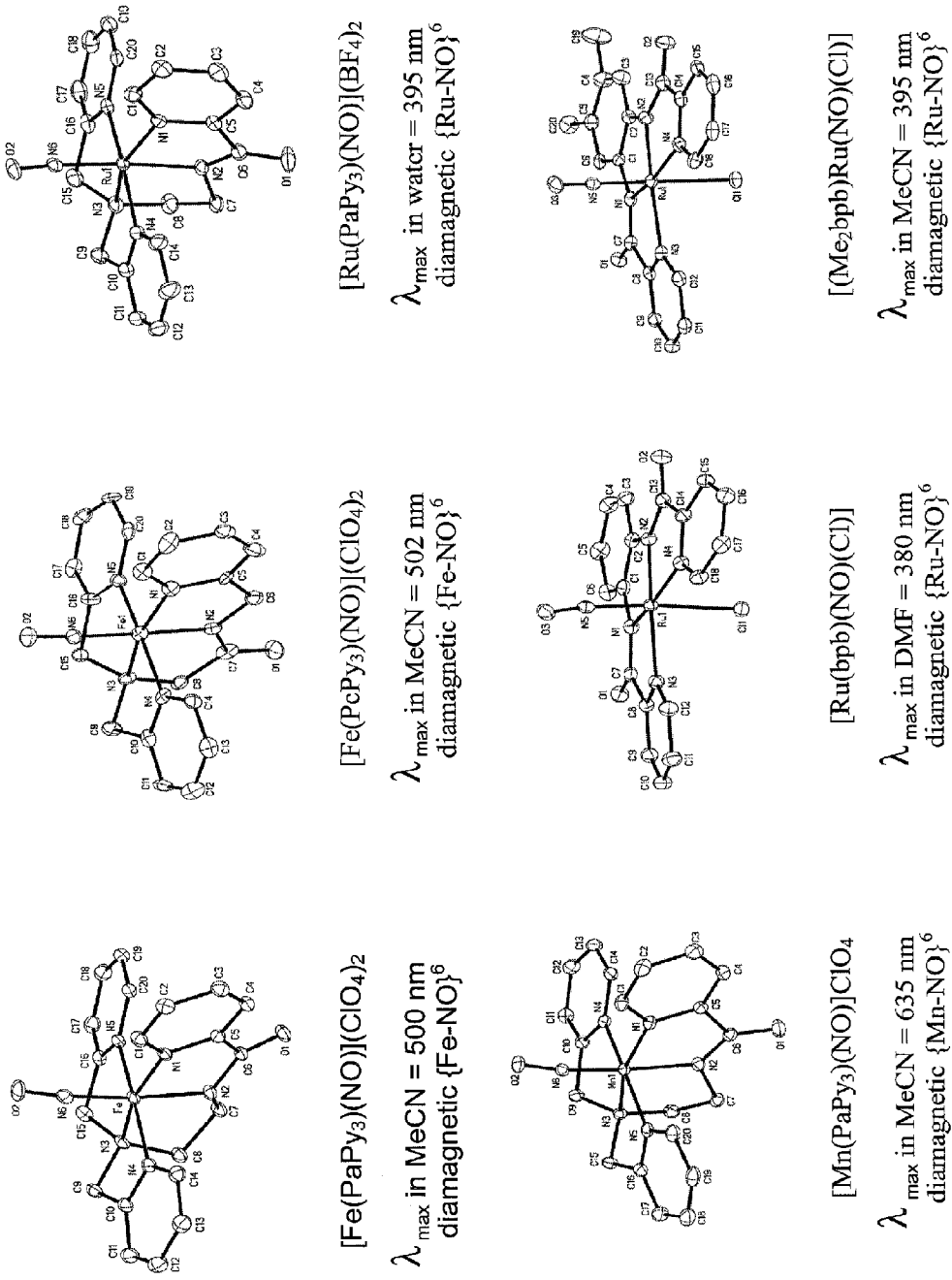
FIG. 6 shows structures of several metal nitrosyls with photolabile NO that have been synthesized by the inventor.
Figure 7:
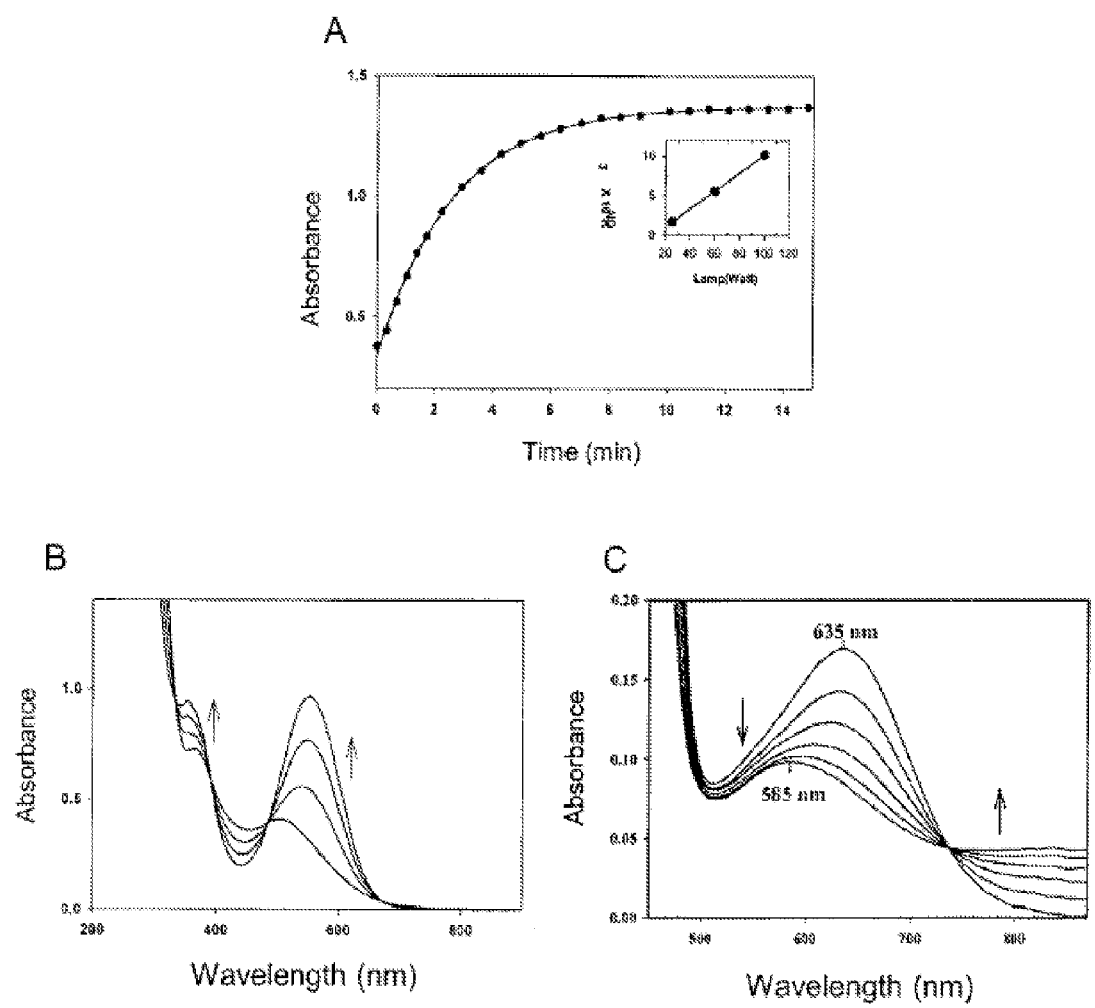
FIG. 7 B provides a graph showing the conversion of $[(PaPy_3)Fe(NO)](ClO_4)_2$ (bottom trace) into the MeCN-adduct (top trace) in MeCN following NO loss under illumination with a 50 W tungsten lamp ($t_{1/2}$=45 s; Patra et al., *Angew Chem Int Ed*, 41:2512-2515, 2002, herein incorporated by reference).

As described herein, nitrosyls like [Fe(PaPy$_3$)(NO)](ClO$_4$)$_2$ and [Mn(PaPy$_3$)(NO)](BF$_4$)$_2$ are converted into the corresponding solvato species [M(PaPy$_3$)(solv)]$^{2+}$ following NO loss. Clean isosbestic points in the multiple trace spectra (e.g., FIG. 6B and FIG. 6C) indicate that the [M(PaPy$_3$)(NO)]$^{2+}$→[M(PaPy$_3$)(solv)]$^{2+}$ transformation is likely devoid of other intermediates. So far, the light reactions with the nitrosyls complexes appear to be very clean unlike the light reactions with Roussin's salts.[12] It is also important to note that unlike the Heme-NO species,[12] the inventive metal nitrosyls do not suffer from any significant back reaction (e.g., NO recombination) since the metal site, preferably a M$^{3+}$ site, often prefers solvents such as MeCN and H$_2$O as the sixth ligand over NO. Preliminary actinometric measurements have afforded a quantum yield of 0.12 for the light reaction of [Ru(PaPy$_3$)(NO)](BF$_4$)$_2$ in water. Collectively, these properties indicate that the nitrosyl complexes disclosed herein are good light-induced NO donors.

The low power of light used in these studies is noteworthy. Inorganic NO donors known in the art require either high power laser light or 500 xenon arc lamp for NO release. In contrast, the metal nitrosyls of the present invention release NO upon illumination with low power light, including less than 100 W, 60 W, or 50 W, and also with less exotic sources of light, such as a tungsten lamp, although laser, halogen and other sources may also be used.

The use of designed ligands (such as those illustrated in FIGS. 4 and 5) makes it possible to synthesize a series of metal nitrosyls that exhibit absorption maxima at different wavelengths (preferably lying in the region from about 900 nm to about 350 nm, including about 850 nm, 800 nm, 750 nm, 700 nm, 650 nm, 600 nm, 550 nm, 500 nm, 450 nm and 400 nm). Complexes having absorption maxima at wavelengths above and below these values, and at any of the values between the specific numbers noted above are also contemplated. Thus the present invention provides a collection of non-porphyrin NO donors that can be activated with light of various wavelengths.

The light characteristics of any one of these metal nitrosyls can be changed (tuned) with minor alterations in the ligand frames such as changing a donor atom or ring size. This is a tremendous advantage of the present approach, thereby freeing users of this technology from the light requirements of photoactive nitrosyls of the prior art, which hereto have been found serendipitously. As an illustration, [Fe(PaPy$_3$)(NO)] (ClO$_4$)$_2$ has been found to release NO when illuminated with ~500 nm light, while [Ru(PaPy$_3$)(NO)](BF$_4$)$_2$ releases NO only under UV light ($\lambda$<350 nm).

V. Ability to Move Absorption Maximum ($\lambda_{max}$)

Figure 8:
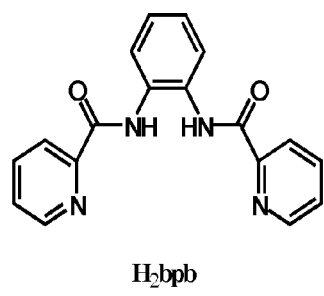
FIG. 8(A) shows the structure of the designed ligand $H_2$bpb.
FIG. 8(B) shows the structure of the designed ligand $H_2Me_2$bqb.
FIG. 8(C) provides a plot of the electronic absorption spectrum of $[(bpb)Ru(NO)(Cl)]$ (broken line) and $[(Me_2bqb)Ru(NO)(Cl)]$ (solid line) in DMF. Both nitrosyls are photolabile. $[(bpb)Ru(NO)(Cl)]$ releases NO upon illumination with UV light ($\lambda_{max}$ 350 nm), while $[(Me_2bqb)Ru(NO)(Cl)]$ releases NO upon illumination with visible light (Patra et al., Inorg Chem, 43:4487-4495, 2004, herein incorporated by reference. Use of UV-cut filters confirms that the latter complex is sensitive to visible light.
Figure 8:
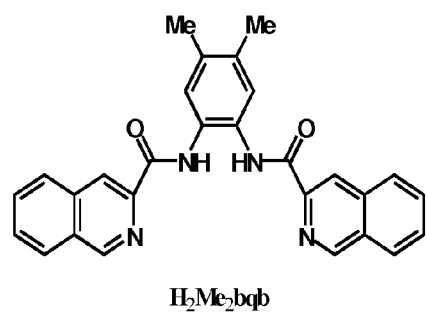
Figure 8:
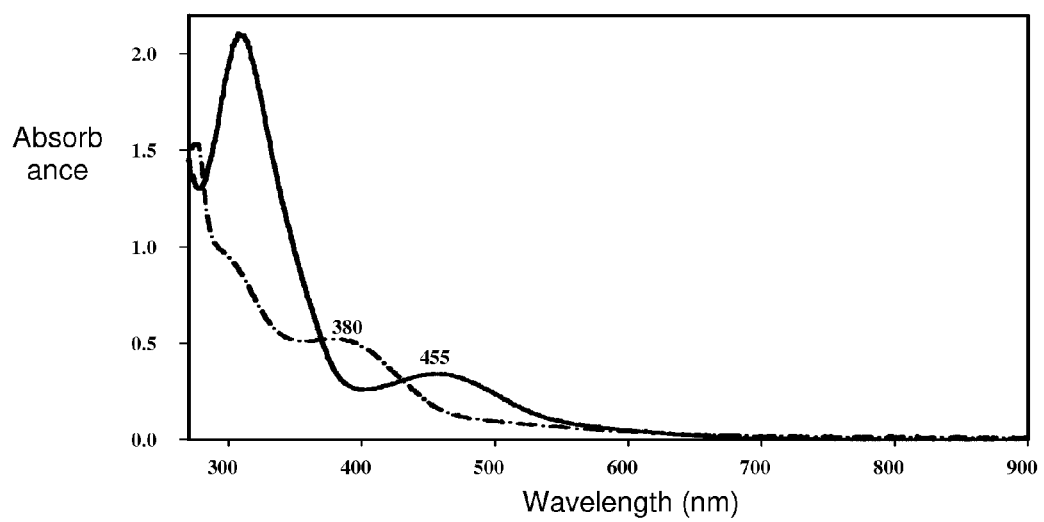

The systematic approach of the present invention allows one to alter the ligand frame to bring the absorption maximum ($\lambda_{max}$) to any desired region and test the photolability of the bound NO. For drug use, one prefers NO donors that release NO upon illumination in the visible range. The following example demonstrates that minor alterations move $\lambda_{max}$ of these metal nitrosyls from UV to the visible region. The complex [Ru(bpb)(NO)(Cl)] (derived from the designed ligand H$_2$ bpb) exhibits its $\lambda_{max}$ in MeCN at 380 nm. In order to move this absorption maximum more to the visible region, the complex [Ru(Me$_2$bqb)(NO)(Cl)] (derived from the designed ligand H$_2$Me$_2$bqb) has been synthesized. As shown in FIG. 8, the new ligand H$_2$Me$_2$bqb contains quinaldic acid moiety in place of picolinic acid moiety in the bpb ligand. This change in the ligand frame causes a shift in the $\lambda_{max}$ from 380 nm (in case of complex [Ru(bpb)(NO)(Cl)]) to 455 nm (in case of [Ru(Me$_2$bqb)(NO)(Cl)]), as shown in FIG. 8C.

In another embodiment, 9,10-diaminophenanthrene is used instead of o-diaminobenzene to add more conjugation in the ligand system. It is contemplated that such an alteration is suitable for moving the $\lambda_{max}$ of the resulting ruthenium nitrosyl further into the visible region (additional details are provided in Patra et al., *Inorg Chem*, 12:4487-4495, 2004, herein incorporated by reference).

VI. Photoactive Metal Nitrosyls as Convenient Nitrosylating Agents for Proteins

Binding of NO to Myoglobin (Mb) and Hemoglobin (Hb), a process that regulates a variety of biological responses including blood pressure regulation and platelet aggregation is well known in the art. Inhibition of heme proteins such as cytochrome c oxidase and non-heme proteins such as lipoxygenase by NO has also been studied. It is now known that binding of NO to cytochrome c oxidase modulates mitochondrial respiration, while 15-lipoxygenase catalytically consumes NO and impairs activation of guanylate cyclase. In all such studies, both NO gas and NO donors such as GTN and GSNO have been employed.

The present set of nitrosyls as disclosed herein can be used as novel NO donors having one or more attractive properties. One property is that the delivery of NO and thus the nitrosylation reaction, can be controlled and triggered at ease by light exposure at selected frequencies, chosen from among a wide range of possible wavelengths depending upon ligand choice and design. Furthermore, because the nitrosylating agent is a solid, it can be measured easily for stoichiometric studies, unlike NO gas.

Figure 9:
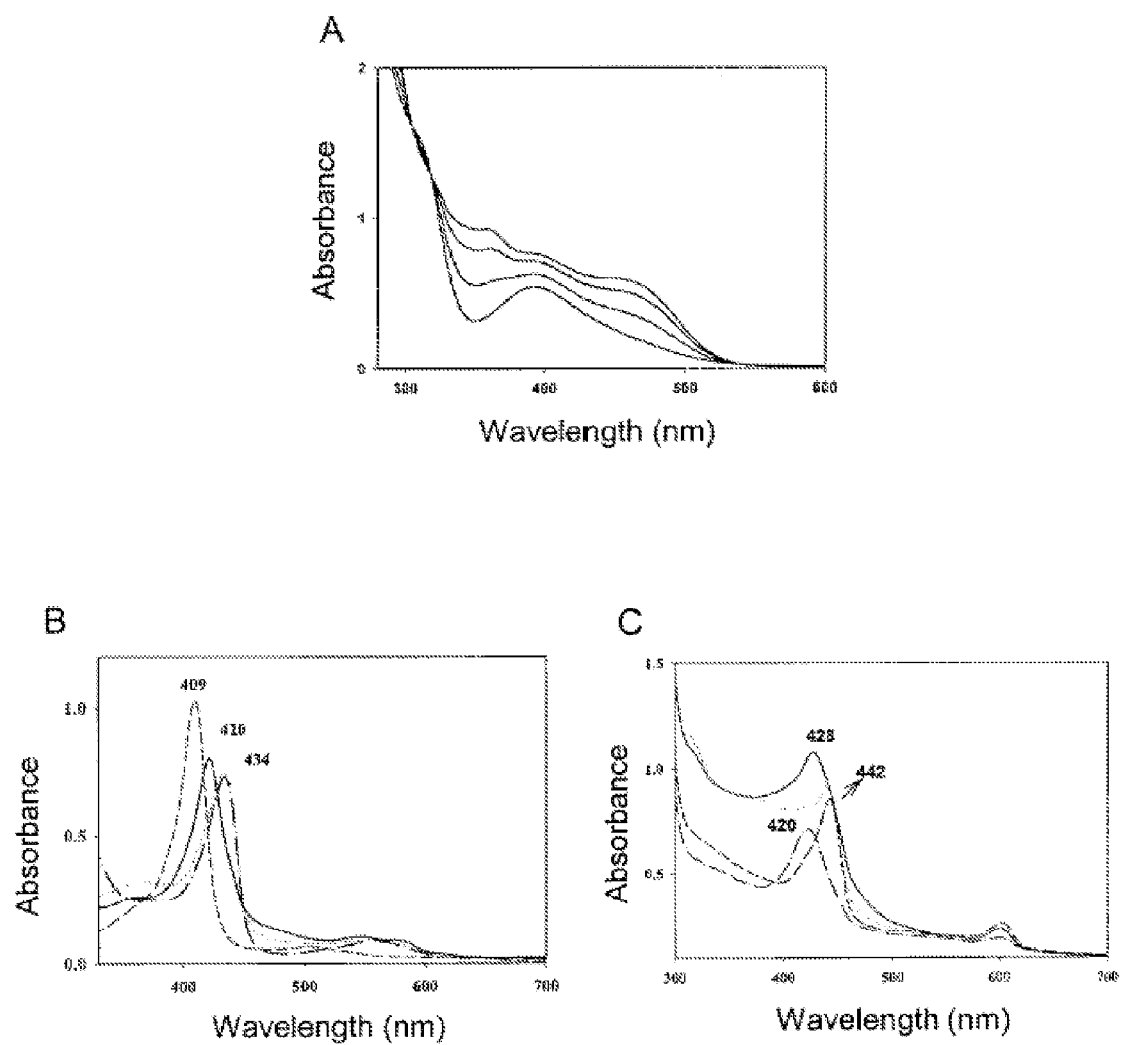
FIG. 9(A) shows conversion of $[(PaPy_3)Ru(NO)]^{2+}$ (bottom trace, $\lambda_{max}$=395 nm) into $[(PaPy_3)Ru(H_2O)]^{2+}$ (top trace, $\lambda_{max}$=455, 400 and 355 nm) in aqueous solution under low intensity UV light ($t_{1/2}$=3 min).
FIG. 9(B) shows conversion of reduced Mb to Mb-NO upon reaction with $[(PaPy_3)Ru(NO)](BF_4)_2$ in aqueous solution upon exposure to low intensity UV light. Dashed line: met-Mb; dash-dot line: reduced Mb; dotted line: a mixture of $[(PaPy_3)Ru(NO)](BF_4)_2$ and reduced Mb (1.5:1) under ordinary light (20 min); solid line: same mixture exposed to UV(30 s).
FIG. 9(C) shows conversion of reduced cyt c oxidase to its NO-adduct via reaction with $[(PaPy_3)Ru(NO)](BF_4)_2$ under low intensity UV light. Dash-dot line: oxidized and dash line: reduced enzyme; dotted line: reduced enzyme plus $[(PaPy_3)Ru(NO)](BF_4)_2$ under ordinary light (20 min); solid line: same mixture exposed to UV light for 30 s (Patra and Mascharak, *Inorg Chem*, 42:7363-7365, 2003, herein incorporated by reference).

As shown in FIG. 9A, exposure of an aqueous solution of [Ru(PaPy$_3$)(NO)](BF$_4$)$_2$ to low intensity UV light (5 mW; $\lambda_{max}$ 305 nm) light results in release of NO and formation of the aqua complex [Ru(PaPy$_3$)(H$_2$O)](BF$_4$)$_2$. When this process is repeated in presence of reduced Mb, the 434 nm Soret band of reduced Mb is rapidly changed to 420 nm indicating formation of the Mb-NO adduct (FIG. 9B). Clearly [Ru(PaPy$_3$)(H$_2$O)](BF$_4$)$_2$ acts as an efficient NO donor that is activated by light. Similar results have been obtained with cytochrome c oxidase. Exposure of a mixture of [Ru(PaPy$_3$)(H$_2$O)](BF$_4$)$_2$ and reduced cytochrome c oxidase to UV light rapidly generated the NO adduct (Soret band at 428 nm, FIG. 9C). These results confirm that the metal nitrosyls such as [Ru(PaPy$_3$)(H$_2$O)](BF$_4$)$_2$ described herein are suitable for use as NO donors that can be activated with light. Other compounds according to the disclosure herein are known to, or are predicted to, have similar results with regard to being able to facilitate NO transfer to Mb and Hb.

VII. Administration of Non-Porphyrin Metal Nitrosyls

In accordance with preferred embodiments, nitrosylation complexes as are delivered or administered and then activated by light to cause release of NO. In therapeutic methods, a pharmaceutically effective amount of a complex (including a combination of one or more complexes) is delivered or administered and then activated by application of light corresponding to the absorption maximum required for efficient NO release by the complex of interest.

The delivery rate of NO is controlled by the duration, intensity, and/or frequency of light delivered, as well as by the amount of complex present. The control of the spatial component of NO delivery is effected by site-specific delivery of the complex and/or by site-specific delivery of the activating light, in some embodiments. Site-specific delivery of at least one complex (e.g., one or more metal nitrosyl species) is accomplished by direct injection or application, such as by a syringe, catheter, transdermal patch, topical application, endoscopic application or implantation, as well as by other means such as those known in the art. Site-specific delivery of light is most easily accomplished by directing the light to a specific region of the body whether externally by directing illumination of an external source to a part of the body, or internally by use of catheter-based, endoscopic, and/or fiberoptic sources, as are well known in the art. Fully or partially implanted temporary, permanent or semi-permanent light sources, such as may be made using fiber optics or other sources, are also contemplated. Site-specific light delivery is also done by masking or shading areas outside of a target area. Light for activation may be of any variety and from any kind of source, including generally monochromatic light, full spectrum light, and/or light having a specific collection of wavelengths or one or more portions of the spectrum, and may come from a laser, LED, incandescent source, or any source as is known in the art.

Site-specific delivery of a complex may also be done by implanting or administering a device that has been coated or impregnated with a material comprising a complex. For example, a vascular stent having a coating comprising a complex may be implanted in a blood vessel, or a device such as a seed, capsule, or packet comprising a complex may be implanted or delivered to a site within the body, such as a tumor or organ. The metal nitrosyls derived from ligands with vinyl benzene side arm ($R^4{}_n$=vinyl benzene in FIG. 4) can be impregnated into a polymer matrix by standard template copolymerization methods with the use of methyl acrylate, azobisisobutyronitrile (AIBN) in 1,2-dicholobenzene under argon (see for example, Sellergren, B. Ed. "Molecular Imprinted Polymers: Man-Made Mimics of Antibodies and their Applications in Analytical Chemistry" Elsevier: Amsterdam, 2001). Beads of such polymer can be placed in the desired locale and irradiated by using light via fiber optics. Once implanted, the device can serve as a source or reservoir of complex for use in one or more treatment periods in which light is administered and NO delivered. Similarly, a catheter may be fitted with a tip or other portion comprising a complex, or be used in combination with a separate element, such as a guidewire comprising a complex, which can be used in combination with a light source (external or internal) to effect site-specific delivery of NO. A catheter having ports or pores through which a fluid may be expressed, as are well known in the art, may also be used to deliver a complex.

The foregoing methods of delivering NO may be used to treat any condition, disease, or ailment for which NO has therapeutic value. For example, delivery of NO to smooth muscle results in relaxation of that smooth muscle. If the smooth muscle is in a blood vessel, such as an artery, relaxation of the muscle will result in vasodilation and a reduction in blood pressure. The relaxation of smooth muscle is the result of NO release triggered by light activation, and results in the lowering of blood pressure in a mammal when the smooth muscle comprises a blood vessel, such as an artery, of the mammal. The vasodilative properties of NO delivered via a complex are also useful for treating sexual dysfunction, including erectile dysfunction. Delivery or application of a complex to the tissues of the genital area, followed by application of light to induce NO release can alleviate the symptoms of sexual dysfunction. Alternatively, NO is well known as a toxic material, and thus delivery of NO may also be used to kill cells, including tumors, pre-cancerous tissue, and other undesirable tissues.

Therapeutic applications employing the metal nitrosyl complexes according to preferred embodiments disclosed herein may use formulations such as solutions or suspensions, or the complexes may be utilized in compositions such as tablets, capsules or elixirs for oral administration, suppositories, sterile solutions or suspensions for injectable or parenteral administration, and the like, or incorporated into shaped articles. Subjects in need of treatment (typically mammalian) using the compounds according to the present disclosure can be administered dosages that will provide therapeutic efficacy. The dose and method of administration will vary from subject to subject and may be dependent upon such factors as sex, weight, diet, concurrent medication, overall clinical condition, the particular compounds employed, the specific use for which these compounds are employed, and other factors which those skilled in the medical arts will recognize.

Formulations including the complexes disclosed herein are prepared for storage or administration by mixing the complex, or a pharmaceutically acceptable salt, solvate or prodrug thereof, having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counter ions such as sodium and/or nonionic surfactants such as Tween, Pluronics or polyethyleneglycol.

Dosage formulations of the present compounds to be used for parenteral administration are preferably sterile. Sterility is readily accomplished by filtration through sterile membranes such as 0.2 micron membranes, or by other conventional methods known to those skilled in the art. Formulations are preferably stored in lyophilized form or as an aqueous solution. The pH of the preparations fall preferably between 3 and 11, including from 5 to 9, and from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds according to the present disclosure are desirably incorporated into shaped articles such as implants, which may employ inert materials such as biodegradable polymers or synthetic silicones, for example, Silastic, silicone rubber or other polymers commercially available.

The complexes according to the present disclosure may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The complexes according to the present disclosure may also be delivered by the use of antibodies, antibody fragments, growth factors, hormones, or other targeting moieties, to which the compound molecules are coupled. The complexes may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, the complexes disclosed herein may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic liquid formulations generally are placed into a container having a sterile access port, for example, an intravenous solution bag or vial having a stopper pierceable by hypodermic injection needle, or, in some cases, they may be administered orally.

Therapeutically effective dosages may be determined by either in vitro or in vivo methods. For each particular compound presently disclosed, individual determinations may be made to determine a suitable dosage. The range of therapeutically effective dosages will naturally be influenced by the route of administration, the therapeutic objectives, and the condition of the patient. For injection by hypodermic needle, it may be assumed the dosage is delivered into the body's fluids, but it often is delivered to a target tissue by use of a catheter or endoscopic delivery system. For other routes of administration, the absorption efficiency should be determined for each compound by methods well known in pharmacology. Accordingly, it may be necessary for the therapist to titer the dosage and modify the route of administration as required to obtain a desired therapeutic effect. The determination of effective dosage levels, that is, the dosage levels necessary to achieve the desired result, will be within the abilities of one skilled in the art. Typically, applications of the complex are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the complexes disclosed herein may be administered several times daily, and other dosage regimens may also be useful.

Typically, about 0.5 to 500 mg of a complex or mixture of complexes, as the free acid or base form or as a pharmaceutically acceptable salt, is compounded with one or more of a physiologically acceptable vehicle, carrier, excipient, binder, preservative, stabilizer, dye, flavor etc., as called for by accepted pharmaceutical practice. The amount of active ingredient in these complexes is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods disclosed herein, the complexes may be used alone or in combination, or in combination with other therapeutic or diagnostic agents. In certain preferred embodiments, the complexes disclosed herein may be co-administered along with other compounds or complexes. The complexes disclosed herein can be utilized in vivo, ordinarily in mammals such as primates, such as humans, sheep, horses, cattle, pigs, dogs, cats, rats and mice, or in vitro.

In addition to the therapeutic applications noted above, complexes may also be used in much the same manner in diagnostic applications. For example, a complex may be prepared using labeled NO which would then allow for delivery of labeled NO for diagnostic or scientific study of how NO is used in a cell, tissue, or body.

These compounds also have utility as convenient nitrosylating agents for proteins. Presently, people use NO gas for such nitrosylations. Since one can trigger the NO release by light of selected wavelengths, researchers will be able to use these solid and stable compounds in quantitative measurements using light of their choice. Use of the inventive complexes is also advantageous because of troubles arising from handling NO gas such as its toxicity, its uncontrollable diffusion, and the need for purification for precise experiments, will be absent when researchers employ these compounds as the NO-donors.

DEFINITIONS

The term "alkyl" refers to saturated and unsaturated aliphatic groups including straight-chain and branched-chain and cyclic groups, or any combination thereof, having the number of carbon atoms specified, or if no number is specified, having up to 12 carbon atoms, but preferably having one to three carbon atoms. Cyclic alkyls typically comprise a monocyclic aliphatic ring having 3 to 12 carbon atoms and preferably 3 to 7 carbon atoms. The cyclic alkyls of this invention may include one or more nitrogen atoms. Preferably, "alkyl" refers to straight-chain and branched-chain groups; more preferably saturated straight-chain groups.

The term "alkoxy" refers to a group having the formula —OR where R is alkyl, as defined above.

The term "aryl" refers to an unsubstituted or substituted aromatic ring, substituted with one or more substituents selected from alkyl, alkoxy, nitro, cyano, halo, hydroxy, mercapto, thioalkoxy, carboxyl, amino, alkyl-substituted amino, including but not limited to carbocyclic aryl, heterocyclic aryl, and biaryl groups and the like, all of which may be optionally substituted. Preferred aryl groups include phenyl, naphthyl, biphenyl, phenanthrenyl, naphthacenyl, and other aromatic heterocyclics. The term "heteroaryl" as used herein refers to any aryl group, containing from one to four heteroatoms, selected from the group consisting of nitrogen, oxygen and sulfur.

The term "prodrug derivatives" refers to compounds of the invention that have metabolically cleavable groups and become, by sovolysis or under physiological conditions, compounds of the invention that are pharmaceutically-active in vivo (See Bundgard, H., "Design of Prodrugs", pp. 7-9, 21-24, Elsevier, Amsterdam, 1985).

In the compounds of this invention, carbon atoms bonded to four non-identical substituents are asymmetric. Accordingly, the compounds may exist as stereoisomers, including enantiomers and diastereomers. The compounds of this invention having one or more centers of asymmetry may exist as enantiomers or mixtures thereof (e.g. racemates). In addition, compounds that have two or more asymmetric centers can exist as diastereomers. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using methods known in the art (See for example, Jacqes, Collet and Wilen "Enantiomers, Racemates and Resolutions," Krieger Publishing Co., Malabar, Fla. 1991).

As used herein, the terms "radiant power" and "radiant flux" refer to radiant energy per unit time, as measured in watts. In some embodiments, when a visible light source is employed, the term "low radiant power" corresponds to less than 500 Watts, preferably less than 250 watts. In further embodiments, when an ultraviolet light source is employed, the term "low radiant power" corresponds to less than 100 mWatts, preferably less than 50 mWatts.

The term "visible" light refers to electromagnetic radiation of a wavelength that is can be seen or detected by the human eye. As used herein, the term "visible" light refers to light with a wavelength from 380 to 780 nm.

The terms "ultraviolet light" and "UV light" refer to electromagnetic radiation of a wavelength shorter than that of the visible region, but longer than that of soft X-rays. In particular, terms "long wave" UVA light or "blacklight" refer to light with a wavelength in the range of 380-315 nm. The term "medium wave" UVB light refers to light with a wavelength in the range of 315-280 nm. The terms "short wave" UVC light or "germicidal" light refer to light with a wavelength in the range of 280-10 nm.

As used herein, the term "porphyrin" refers to a heterocyclic macrocycle made from four pyrrole subunits linked on opposite sides through four methine bridges. Porphyrins readily combine with metals coordinating them in the central cavity. Some iron containing porphyrins are termed "hemes."

As used herein, the term "metal nitrosyl" refers to metal complexes containing one or more NO as ligands.

As used herein, the term "pentadentate ligand" refers to organic molecules that bind transition metal ions at five coordination positions via donor atoms such as O, N, S and P. The term "tetradentate ligand" as used herein refers to organic molecules that bind transition metal ions at four coordination positions via donor atoms such as O, N, S, and P.

As used herein, the term "carboxamido group" refers to a C(=O)—NH2 moiety.

As used herein, the term "pyridine ring" refers to a pyridyl group attached to the ligand frame.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: U (units); N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); FBS (fetal bovine serum); and PBS (phosphate buffered saline).

Example 1

Use of Photoactive Metal Nitrosyls for cGMP Production and Smooth Muscle Relaxation Measurement of Soluble Guanyl Cyclase (sGC) Activity
Soluble guanyl cyclase (sGC) activity was determined by measuring the conversion of GTP to cGMP in the absence and presence of the NO-donors of the present invention (Murad et al., "Guanylate Cyclase: Activation by Azide, Nitro Compounds, Nitric Oxide, and Hydroxyl Radical and Inhibition by Hemoglobin and Myoglobin," in *Adv. Cyclic Nucleo. Res*, George and Ignarro (eds.), Raven Press: New York, Vol. 9, 145-158, 1978). Briefly, isolated enzyme (~0.2 μg protein) was incubated in reaction buffer (50 mM triethanolamine-HCl, pH 7.4) containing IBMX (1 mM), phosphocreatine (5 mM), creatine kinase (5 U/mL), MgCl$_2$ (4 mM), BSA (1 mG/mL), dithiothreitol (1 mM) and GTP (2 mM) at 37° C. for 10 minutes. The reaction was terminated by the addition of 50 mM ice-cold sodium acetate (pH 4) and then heating at 95° C. for 3 minutes. Cyclic GMP accumulation was measured using a commercially available ELISA kit (Amersham Biosciences) as per the manufacturer instructions.
cGMP Generation in Cultured Rat Aortic Smooth Muscle Cells Primary rat aortic smooth muscle cells were cultured and exposed to increasing log doses of Ru—NO with and without a 5 minute exposure to low-intensity UV light ($\lambda_{max}$=254 nm) followed by a 10 minute incubation. The cells were then lysed and the cGMP production was assayed Cyclic GMP accumulation was measured using a commercially available ELISA kit (Amersham Biosciences) as per the manufacturer instructions.

Figure 10:
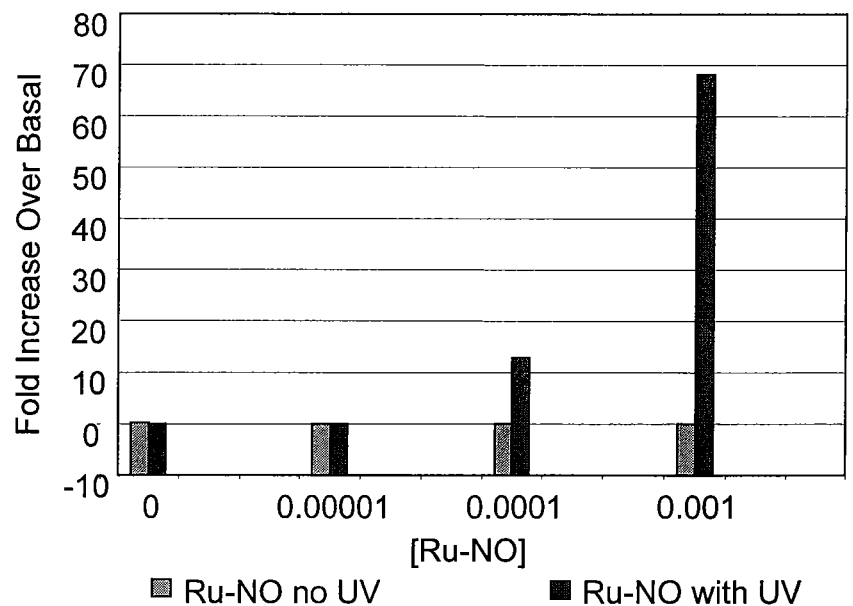
FIG. 10(A) provides a graph showing production of cGMP in rat aortic smooth muscle cells upon $[(PaPy_3)Ru(NO)](BF_4)_2$ treatment, following exposure to light.
FIG. 10(B) provides a graph showing relaxation of rat aortic rings upon exposure to $[(PaPy_3)Ru(NO)](BF_4)_2$ and exposure to UV light. Note the relaxation effect when the Ru-drug concentration goes to $1\times10^{-5}$ M. Although the control drug DEA/NO shows relaxation effect at $1\times10^{-8}$ M, the Ru-drug exhibits the effect only under exposure to light.
Figure 10:
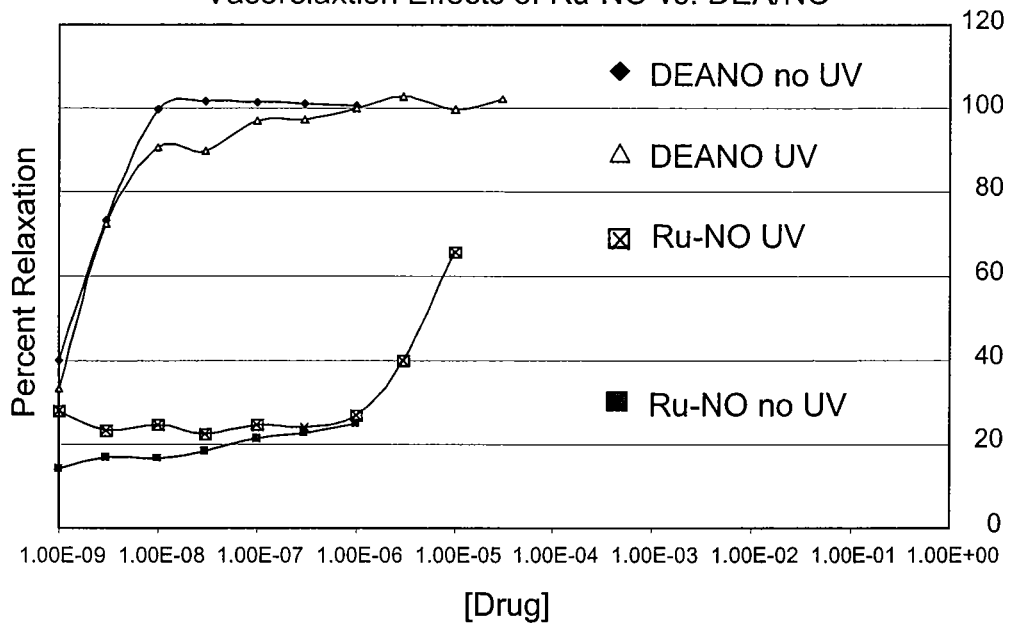

The vasodilation effect of NO is connected to the production of cGMP in the smooth muscle cells. Results of preliminary experiments with [(PaPy$_3$)Ru(NO)](BF$_4$)$_2$ demonstrate that these nitrosyls promote cGMP production in cultured rat aortic smooth muscle cells upon exposure to low-intensity UV light ($\lambda_{max}$=254 nm) for as little as 5 min (due to NO release). Photorelease of NO (and associated increase in cGMP concentration) was not observed in the dark (FIG. 10A). Clearly, the nitrosyl enters the cell and causes cGMP production by releasing NO upon illumination. A dose of 0.1 mM Ru nitrosyl produced a 13-fold increase in cGMP production in an exemplary experiment reported.
Relaxation of Rat Thoracic Aorta Rings Male rats (200-250 g; Sprague-Dawley) were stunned and killed by cervical dislocation. The thoracic aortas were carefully removed, cleaned of connective tissue and cut into 3-4 ring segments of approximately 4 mm in length. Aortic rings were mounted in 10 mL organ baths containing Krebs-bicarbonate buffer (composition (mM): Na$^+$ 143; K$^+$ 5.9; Ca$^{2+}$ 2.5; Mg$^{2+}$ 1.2; Cl$^-$ 128; HCO$_3^-$ 25; HPO$_4^{2-}$ 1.2; SO$_4^{2-}$ 1.2; D-glucose 11) maintained at 37° C. and gassed with 95% O$_2$/5% CO$_2$. Tension was initially set at 1 g and reset at intervals following an equilibrium period of 1 hour during which time fresh Krebs-bicarbonate buffer was replaced every 15-20 minutes. After equilibrium, the rings were primed with KCl (4.8×10$^{-2}$ M) before a supramaximal concentration of phenylephrine (PE; 10$^{-6}$ M) was added. Once this response had stabilized, acetylcholine (ACH; 10$^{-6}$M) was added to the bath to assess the integrity of endothelium of WT vessels. If the contractions to PE were not maintained, or relaxations greater than 50% of the PE-induced tone to ACH were not observed, the tissues were discarded.

Tissues were then washed for 30 minutes (by addition of fresh Krebs-bicarbonate buffer at 15 minutes intervals) after which cumulative concentrations of PE (10$^{-9}$-10$^{-6}$ M) were added to the organ bath. The tissues were then washed over 60 minutes to restore basal tone before contracting to approximately 80% of the maximum PE-induced response. Once a stable response to PE was achieved, cumulative concentration-response curves to the NO-donors were constructed in the presence and absence of light (foil-covered organ baths versus fiber-optic halogen lamp [250 W]) and the soluble cGMP inhibitor ODQ (5 mM).

Rat aortic rings precontracted with phenylephrine exhibited relaxation when the tissue was exposed to UV light in the presence of [(PaPy$_3$)Ru(NO)](BF$_4$)$_2$. The relaxation was comparable to that observed upon treatment of the tissue with a conventional NO donor (DEA/NO) as shown in FIG. 10B. Significant contraction was observed with a dose of 1×10$^{-5}$ M of the Ru nitrosyl. When the light was turned off, the tissue contracted ~25%. When the light was turned on again, the tissue relaxed to its final value. This illustrates very nicely the light dependence of NO release from the metal nitrosyls of the present invention, as well as the associated tissue relaxation.

Collectively, these results demonstrate that the metal nitrosyls described herein are suitable NO donors for achieving muscle relaxation (and blood pressure reduction) under light. One can achieve both in vivo muscle relaxation and lowering of blood pressure by raising the local concentration of one of these nitrosyls (selection will depend on the solubility, stability and toxicity of the compound) followed by exposure of light (of selected wavelengths or broad spectrum), such as via fiber optics.

Example 2

Use of Metal Nitrosyls as Agents for Photodynamic Therapy for Cancer

Conventional photodynamic therapy (PDT) utilizes reactive oxygen species (ROS) for killing cells[13], including the treatment of cancer.[14] In fact, the U.S. Food and drug Administration has already approved photodynamic therapy (PDT) with PHOTOFRIN (a porfimer sodium composition available from Axcan Scandipharm, Inc.) for the treatment of esophageal, bladder, head and neck, and skin cancers and some stages of lung cancers. Singlet oxygen is however not the only agent for such selective cell kill. The production of endogenous NO has recently been shown to be associated with apoptosis of tumorigenic cells (Xu et al., Cell Res, 12:311-320, 2002; and Wink et al., Carcinogenesis, 19:711-721, 1998). Sudden increases in NO concentration (mM or higher) initiate apoptosis, characterized by changes in the expression of pro- and anti-apoptotic Bcl-2 family members, cytochrome c relocation, activation of caspases, chromatin condensation and DNK fragmentation (Vega et al., Mol Human Reprod, 6:681-687, 2000; and Brune et al., Eur J Pharmacol, 351: 261-272, 1998). These results suggest the possibility that production of endogenous NO could be detrimental to tumor cell survival.

Administration of thermal NO-donors however is undesirable due to various systemic side effects. On the other hand, confining the photoactive NO-donors to malignant tissues (solid tumors) and then triggering NO-release by illumination is contemplated to result in a high (pathological) concentration of NO at specific target without adversely affecting other tissues. Since the metal nitrosyls of the present invention are triggered to release NO upon exposure to light of selected wavelengths (including low intensity light), the NO donors described herein are contemplated to be useful in photodynamic therapy for tumors. The NO donors are particularly suitable for use in cases of solid localized tumors, where one can inject the metal nitrosyls and expose the malignant locales to low-intensity light of selected wavelength. Since the nitrosyls release NO only upon exposure to light of different wavelengths (depending on the NO donor structure and composition) the present set of metal nitrosyls provide desirable therapeutic agents for applications involving light-induced destruction of malignant tissues via sudden NO bursts under controlled conditions. For instance, nitrosyl-polymer hybrid pellets can be implanted in tumors (or placed next to the tumor by the use of endoscopes and catheters). Placement of the catheter containing the nitrosyl-polymer hybrid is expected to be comparatively simple since a small amount of NO release from the pellet (via low illumination during insertion) is contemplated to increase the hemocompatibility of the device (high thromboresistivity) (Keefer, Nat Mater, 2:357-358, 2003). Once the NO-donor is in place, the physician triggers NO release at the target area with the help of light (via a fiber optic cable). The sudden increase in NO concentration then leads to destruction of the cancer cells with minimal side effect(s). So far, this kind of local generation of NO has not been possible with the conventional NO-donors. Since the light is provided via a fiber optic cable, light penetration (the common limitation of photochemotherapeutics) should not be a problem. The localized use of polymer-supported metal nitrosyls of the present invention should also eliminate problems associated with toxicity.

Figure 11:
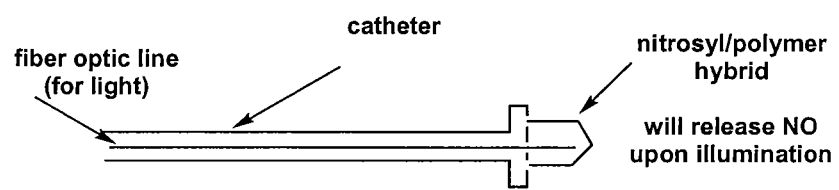
FIG. 11 provides a schematic of a device for depositing a metal nitrosyl/polymer at a specific location in a subject's body.

The ultimate goal of the NO-related drug discovery effort is to devise strategies for selectively delivering NO to the sites of need while avoiding other NO-sensitive parts of the body. In some embodiments, NO-donors are immobilized in a polymer matrix (such as that disclosed in U.S. Pat. No. 6,656,217, herein incorporated by reference). The nitrosyl-polymer hybrid (in the form of pellets) is connected at the end of a catheter and placed in a desired position in a subject's body with the aid of an endoscope. A coaxial fiber optic line is placed alongside the catheter for delivering light for subsequent release of a sudden burst of NO under control of a clinician (e.g., physician, nurse, etc.). The concept is schematically shown in FIG. 11). One will be able to achieve in vivo muscle relaxation (and lowering of blood pressure near constrictions) or target cell kill (in case of malignancy) by raising the local NO concentration temporarily to a high level with this kind of a device. Selection of the metal nitrosyl is influenced by the stability and toxicity of the compound. Since NO is produced locally, adverse effects of NO in other parts of the body are not encountered. With conventional NO donors, any attempt to raise NO levels in a targeted area brings about serious side effects as high dosages of the conventional NO donors must be administered. Since the metal nitrosyls of the present invention do not suffer from the problem of NO recombination, only small amounts of these NO-donors are required to achieve physiologically significant concentrations of NO in the target area(s).

Example 3

Use of Metal Nitrosyls to for Inhibition of a Cysteine Protease

Twice-crystallized papain was activated by stirring the enzyme in 50 mM phosphate buffer (pH 6.2) containing 10 mM dithiothreitol (DTT) for 24 h. The solution was then passed through a Pharmacia 20 mL desalting column equipped with a BioRad FPLC absorbance/electrical-conducting detector at 4° C. The activated protein (devoid of DTT) eluted from the column in 2 minutes at a flow rate of 2 mL/min, and was subsequently lyophilized and stored at −20° C.

Papain Inhibition Studies Using $[(PaPy_3)Mn(NO)](ClO_4)$

Papain activity was determined spectrophotometrically at 410 nm by monitoring the formation of p-nitroaniline from the substrate $N_\alpha$-Benzoyl-l-arginine-p-nitroanilide (l-BApNA). A 1.5 mM stock solution of l-BApNA was prepared in 50 mM phosphate buffer (pH 6.2, 1 mM EDTA, 0.1 M NaCl) and stored at room temperature. A 4.6 µM stock solution of active papain was also prepared in 50 mM phosphate buffer (pH 6.2, 1 mM EDTA, 0.1 M NaCl) and stored at 0° C. Finally, a freshly prepared 3.0 mM stock solution of 1 was prepared in 50 mM phosphate buffer (pH 6.2, 1 mM EDTA, 0.1 M NaCl) and stored in the dark.

To initiate inhibition, 250 µL of active papain was added to 50 µL of a serially diluted solution of $[(PaPy_3)Mn(NO)](ClO_4)$ (final concentration ranged from 0.083 mM-0.500 mM) in the dark in a 650 µL cuvette. The mixture was then exposed to a 50 W tungsten bulb (Afshar at al., Inorg Chem, 43:5736-5743, 2004) for 60 s and 350 µL of the substrate was quickly added. The residual enzyme activity was monitored at 25° C. To measure light dependence on the transfer rate of NO to active papain, the exposure time was varied. The concentrations of the substrate and enzyme were kept the same as above and the final concentration of $[(PaPy_3)Mn(NO)](ClO_4)$ was maintained at 0.167 mM. A 250 µL aliquot of active papain was added to 50 µL of $[(PaPy_3)Mn(NO)](ClO_4)$ and the mixture was exposed to a 50 W tungsten lamp for various time intervals (0 s-90 s). After each exposure, 350 µL of the substrate was added to the solution and the residual enzyme activity was monitored at 25° C.

Separation and Identification of Papain-SNO Adduct Using High-Pressure Liquid Chromatography (HPLC)

A mixture of active papain (3 mg/mL, 1 mL) and $[(PaPy_3)Mn(NO)]ClO_4)$ (3 mM, 1 mL) in 50 mM phosphate buffer (pH 6.2, 0.1 mM EDTA, 0.1 M NaCl) was exposed to a 50 W tungsten lamp for 3 min at 25° C., completely eliminating the enzymatic activity. The protein was then injected into a Spectra-Physics UV 2000 HPLC setup with a Grace VYDAC reverse phase C4 column (10 μm particle size, 4.6×150 mm, 1 mL loop volume). The elution was carried out using the following gradient of H$_2$O-MeCN: 95%:5% H$_2$O:MeCN to 75%:35% H$_2$O:MeCN in 5 min, then to 45%:55% H$_2$O:MeCN in 60 min, and finally to 5%:95% in 3 min. The retention time of both active papain and papain-SNO was 40.7 min under these conditions.

Mass Spectrometry

Electrospray ionization mass spectrometry (ESI-MS) was carried out on a Waters Micromass ZMD mass spectrometer. Protein samples collected from the HPLC were injected directly into the Z-spray source of the MS at a flow rate of 20 μL/min. The instrumental parameters used were as follows: cone voltage 2.80 kV, capillary voltage 30V, multiplier 550V, desolvation temp 110° C., and cone block temp 150° C. The mass spectra were deconvoluted using MaxEnt 1 software (Waters Micromass).

Results

Figure 12:
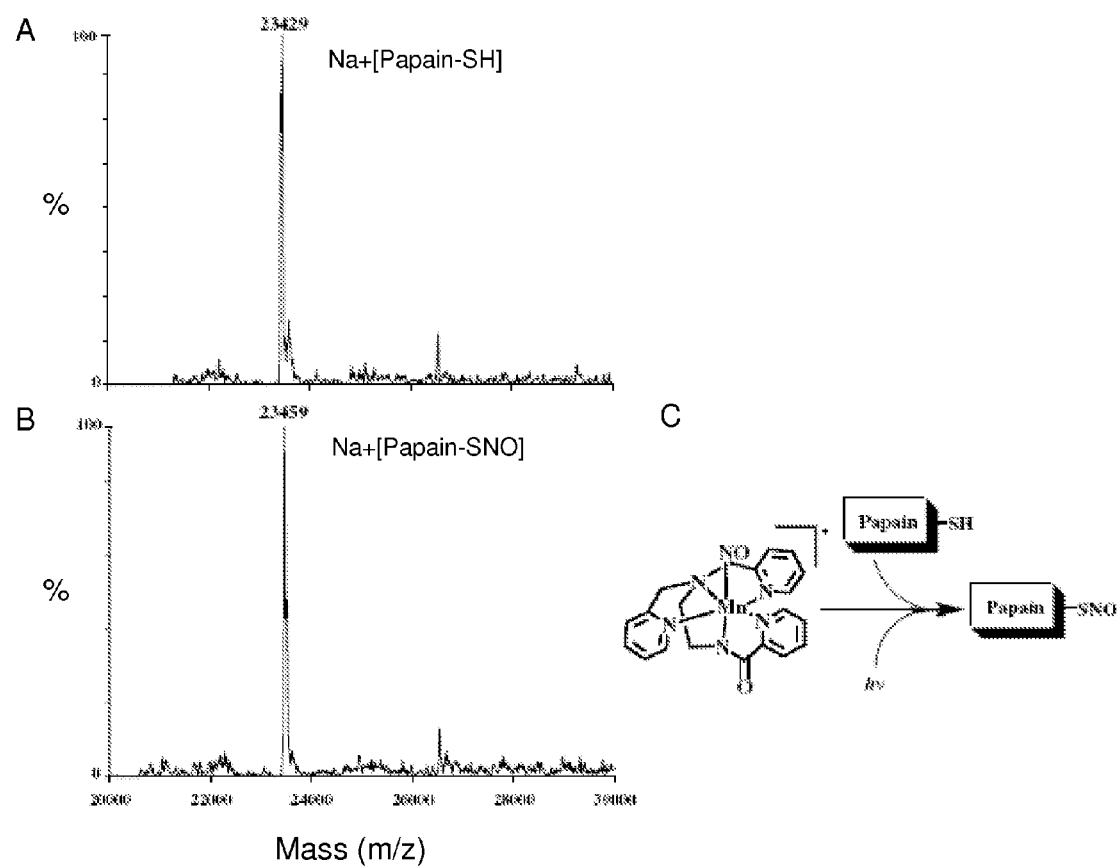
FIG. 12(A) provides a mass spectrum of Na$^+$[papain-SH] protein.
FIG. 12(B) provides a mass spectrum of Na$^+$[papain-SNO] protein showing the addition of 30 mass units indicative of S—NO bound formation.
FIG. 12(C) provides a schematic of S-nitrosylation of papain by $[(PaPy_3)Mn(NO)]^+$.

The formation of the S—NO adduct in papain was confirmed by HPLC-MS. The electrospray mass spectra of native papain (purified by the same HPLC method) and the nitrosylated papain fraction were obtained in the positive ion mode and the m/z values of the parent ions were calculated by the MaxEnt program by Waters. As shown in FIG. 12(A) papain exhibits its molecular ion peak at m/z=23,429. Crystallographic results have assigned a molecular weight of 23,406 to pure papain (Mitchel et al., J Biol Chem, 243:3485-3492, 1970). The difference of 23 m/z corresponds to a Na+ ion that associates with papain in our mass spectrum. The spectrum in FIG. 12(B) displays a molecular ion peak at m/z=23,459 and corresponds to the papain-SNO adduct (a difference of 30 mass units). The peak at m/z=23,459 was also obtained when papain was incubated with GSNO (for 30 min) and the reaction product was analyzed by mass spectrometry following purification by HPLC. In the latter case, the mass spectrum showed peaks for both the papainS-NO (fraction with retention time 40.7 min) and papainS-SG (fraction with retention time 37.2 min) at 393 m/z=23,459 and 23,735, respectively. Identification of the papain-SNO adduct clearly demonstrates that inhibition of papain by [(PaPy$_3$)Mn(NO)](ClO$_4$) under light occurs due to the nitrosylation of the active site cysteine All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims. REFERENCES 1. *Methods in Nitric Oxide Research*; Feelisch M., Stamler, J. S., Eds.; John Wiley and Sons; Chichester, England, 1996 and references therein.
2. Mechanistic Aspects of the Reactions of Nitric oxide with Transition-Metal Complexes. Ford, P. C.; Lorkovic, I. M. *Chem. Rev.* 2002, 102, 993 and references therein.
3. *Nitric Oxide: Biology and Pathobiology*, Ignarro, L. J., Ed.; Academic press: San Diego, 2000.
4. *Nitric Oxide and Infection*; Fang, F. C., Ed.; Kluwer Academic/Plenum Publishers: New York, 1999.
5. NO News is Good news. Koshland, Jr. D. E. *Science,* 1992, 258, 1862.
6. (a) Mechanism of Free-Radical Generation by Nitric Oxide Synthase. Rosen, G. M.; Tsai, P.; Pou, S. *Chem. Rev.* 2002, 102, 1191. (b) Marietta, M. A.; Hurshman, A. R.; Rusche, K. M. *Curr. Opin. Chem. Biol.* 1998, 2, 656. (c) The Surprising Life of Nitric Oxide. Feldman, P. L.; Griffith, O. W.; Stuehr, D. J. *Chem. Eng. News,* 1993, 71, 26.
7. Nitric oxide mediated Photo-induced Cell Death in Human Malignant Cells. Ali, S. M.; Olivo, M. *Internat. J. Oncology* 2003, 22, 751.
8. (a) Nitric Oxide Donors: Chemical Activities and Biological Applications. Wang, P. G.; Xian, M.; Tang, X.; Wu, X.; Wen, Z.; Cai, T.; Janczuk, A. J. *Chem. Rev.* 2002, 102, 1091 and references therein. (b) Non-heme iron Nitrosyls in Biology. Butler, A. R.; Megson, I. L. *Chem. Rev.* 2002, 102, 1155. (c) Chemistry of the Nitric Oxide-Releasing Diazeniumdiolate ("Nitrosohydroxylamine") Functional group and Its Oxygen-Substituted Derivatives. Hrabie, J. A.; Keefer, L. K. *Chem. Rev.* 2002, 102, 1135. (d) New Chemical and Biological Aspects of S-Nitrosothiols. Wang, K.; Zhang, W.; Xian, M.; Hou, Y.-C.; Chen, X.-C.; Cheng, J.-P.; Wang, P. G. *Curr. Med. Chem.* 2000, 7, 821. (e) Current Trends in the Development of Nitric Oxide Donors. Hou, Y.-C.; Janczuk, A.; Wang, P. G. *Curr. Pharm. Design* 1999, 5, 417. (f) Nitric Oxide Complexes of Metalloporphyrins: An Overview of Some Mechanistic Studies. Hoshino, M.; Layerman, L.; Ford, P. C. *Coord. Chem. Rev.* 1999, 187, 75. (g) Chemistry Relevant to the Biological Effects of Nitric Oxide and Metallonitrosyls. Clarke, M. J.; Gaul, J. B. *Struct. Bonding* 1993, 81, 147.
9. Light and Metal Complexes in Medicine. Stochel, G.; Wanat, A.; Kulis, E.; Stasicka, Z. *Coord. Chem. Rev.* 1998, 171, 203.
10. (a) Coordination of Carboxamido Nitrogen to Tervalent Iron: Insight into a New Chapter of Iron Chemistry. Marlin, D. S.; Mascharak, P. K. *Chem. Soc. Rev.* 2000, 29, 69-74. (b) Spin States and Stability of Fe(III) Complexes of Ligands with Carboxamido Nitrogen and Phenolato Oxygen Donors. Marlin, D. S.; Olmstead, M. M.; Mascharak, P. K. *Eur. J. Inorg. Chem.* 2002, 859-865. (c) Chemistry of Iron(III) Complexes of N,N'-bis(2-hydroxyphenyl)-pyridine-2,6-dicarboxamide: Seven-Coordinate Iron(III) Complexes Ligated to Deprotonated Carboxamido Nitrogens. Marlin, D. S.; Olmstead, M. M.; Mascharak, P. K. *Inorg. Chim. Acta,* 2002, 297, 106-114. (d) Carboxamido Nitrogens are Good Donors for Fe(III): Syntheses, Structures, and Properties of Two Low-Spin Nonmacrocyclic Iron(III) Complexes with Tetracarboxamido-N Coordination. Marlin, D. S.; Olmstead, M. M.; Mascharak, P. K. *Inorg. Chem.* 1999, 38, 3258-3260.
11. (a) The First Non-heme Iron(III) Complex with a Carboxamido Group that Exhibits Photolability of a Bound NO Ligand. Patra, A. K.; Afshar, R.; Olmstead, M. M.; Mascharak, P. K. *Angew. Chem. Int. Ed.* 2002, 41, 2512-2515. (b) Iron Nitrosyls of a Pentadentate Ligand Containing a Single Carboxamide Group: Syntheses, Structures, Electronic Properties and Photolability of NO. Patra, A. K.; Rowland, J. M.; Marlin, D. S.; Bill, E.; Olmstead, M. M.; Mascharak, P. K. *Inorg. Chem.* 2003, 42, 6812. (c) A Ruthenium Nitrosyl that rapidly Delivers NO to Proteins in Aqueous Solution Upon Exposure to UV Light. Patra, A. K.; Olmstead, M. M.; Mascharak, P. K. *Inorg. Chem.* 2003, 42, 7363. (d) Reactions of NO with Mn(II) and Mn(II) Center Coordinated to Carboxamido Nitrogen: Synthesis of a Manganese Nitrosyl with Photolabile NO. Ghosh, K.; Eroy-Reveles, A. A.; Avila, B.; Holman, T. R.; Olmstead, M. M.; Mascharak, P. K. *Inorg. Chem.* 2004, 43, 2988. (e) Photolabile Ruthenium Nitrosyls with Planar Dicarboxamide Tetradentate N⁴ Ligands: Effect of In-plane and Axial Ligand Strength on NO Release, Patra, A. K.; Rose, J. J.; Murphy, K.; Olmstead, M. M.; Mascharak, P. K. *Inorg. Chem.* In press.

12. Photochemistry of Metal Nitrosyl Complexes: Delivery of Nitric Oxide to Biological Targets. Ford, P. D.; Bourassa, J.; Miranda, K.; Lee, B.; Lorkovic, I.; Boggs, S.; Kudo, S.; Layerman, L. *Coord. Chem. Rev.* 1998, 171, 185.

13. (a) The History of Photodetection and Photodynamic Therapy. Ackroyd, R.; Kelty, C.; Brown, N.; Reed, M. *Photochem. Photobiol.* 2001, 74, 656. (b) Recent Advances in Photodynamic Therapy. Pandey, R. K. *J. Porphyrins Phthalocyanines* 2000, 4, 368.

14. (a) Photodynamic therapy in Oncology: Mechanisms and Clinical Use. Pass, H. I. *J. natl. Cancer Inst.* 1993, 85, 443. (b) Yearly review: Photochemotherapy of Cancer: Experimental Research. Moan J.; Berg, K. *Photochem. Photobiol.* 1992, 55, 931.

The invention claimed is:

1. A method of synthesizing a non-porphyrin metal nitrosyl having a formula selected from the group consisting of

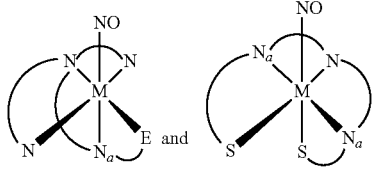

wherein

E is N, O or S, $N_a$ is carboxamido-N;

M is a group 7 or group 8 transition metal in a +2, +3 or +4 oxidation state, and is not $Fe^{II}$, said method comprising:
  a) deprotonating a ligand in a solvent to produce a deprotonated ligand, wherein said ligand is a pentadentate or tetradentate ligand having one or more carboxamido groups;
  b) reacting a metal salt with said deprotonated ligand to produce a solution comprising an intermediate, wherein said metal is group 7 or group 8 transition metal in a +2, +3 or +4 oxidation state; and
  c) passing NO through said solution to produce said non-porphyrin metal nitrosyl.

2. The method of claim 1, wherein said transition metal is selected from the group consisting of $Mn^{II}$, and $Ru^{III}$.

3. The method of claim 1, wherein said ligand is selected from the group consisting of $PaPy_3H$, $PaPy_2OH_2$, $PaPy_2SH_2$, $PcPy_2OH_2$, $PcPy_2SH_2$, $PcPy_3H$, $^{Me}PcPy_3H$, $PaBOH_4$, $PaBSH_4$, $PcBOH_4$, $PcBSH_4$, $Py_2PSH$, $^{Me}PyPSH_4$, $H_2bpb$, and $H_2Me_2bqb$.

4. A method of producing a nitrosylated compound, comprising:
  a) providing a non-porphyrin metal nitrosyl having a formula selected from the group consisting of

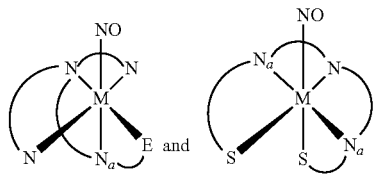

wherein

E is N, O or S, $N_a$ is carboxamido-N;

M is a group 7 or group 8 transition metal in a +2, +3 or +4 oxidation state, and is not $Fe^{II}$,
  b) contacting a compound having a free thiol group with said non-porphyrin metal nitrosyl under conditions suitable for causing S-nitrosylation of said free thiol to produce a nitrosylated compound.

5. The method of claim 4, wherein said conditions comprise maintaining temperature in a range of 4° C. to 42° C.

6. The method of claim 4, wherein said non-porphyrin metal nitrosyl is $[(PaPy_3)Ru(NO)](BF_4)_2$, and said conditions comprise illumination with light of low radiant power, wherein said light comprises ultraviolet light and said low radiant power is in the range of 1 to 50 mWatts.

7. The method of claim 4, wherein said non-porphyrin metal nitrosyl is selected from the group consisting of $[(PaPy_3)Fe(NO)](ClO_4)_2$, $[(PcPy_3)Fe(NO)](ClO_4)_2$, and $[(MePcPy_3)Fe(NO)](ClO_4)_2$, and said conditions comprise an absence of light.

8. The method of claim 4, wherein said compound having a free thiol group is a cysteine protease.

* * * * *